(12) United States Patent
Arai et al.

(10) Patent No.: US 10,405,827 B2
(45) Date of Patent: Sep. 10, 2019

(54) MEDICAL TREATMENT SYSTEM

(71) Applicant: Hitachi, Ltd., Tokyo (JP)

(72) Inventors: Osamu Arai, Tokyo (JP); Naoyuki Murayama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 456 days.

(21) Appl. No.: 15/314,699

(22) PCT Filed: May 11, 2015

(86) PCT No.: PCT/JP2015/063497
§ 371 (c)(1),
(2) Date: Nov. 29, 2016

(87) PCT Pub. No.: WO2015/186475
PCT Pub. Date: Dec. 10, 2015

(65) Prior Publication Data
US 2017/0196535 A1    Jul. 13, 2017

(30) Foreign Application Priority Data
Jun. 4, 2014   (JP) .................................. 2014-115453

(51) Int. Cl.
*A61B 8/00*    (2006.01)
*A61B 8/08*    (2006.01)
(Continued)

(52) U.S. Cl.
CPC .............. *A61B 8/0841* (2013.01); *A61B 8/14* (2013.01); *A61B 8/4254* (2013.01); *A61B 8/466* (2013.01);
(Continued)

(58) Field of Classification Search
CPC ................................ A61B 8/14; A61B 8/0841
See application file for complete search history.

(56) References Cited

U.S. PATENT DOCUMENTS 6,423,009 B1    7/2002  Downey et al.
6,733,458 B1    5/2004  Steins et al.
(Continued)

FOREIGN PATENT DOCUMENTS

CN    1636520 A       7/2005
JP    2006326128 A   12/2006
(Continued)

OTHER PUBLICATIONS

Office Action for the Chinese Patent Application No. 201580029561.7, dated Jan. 16, 2019, 17 pages.
(Continued)

*Primary Examiner* — Joseph M Santos Rodriguez

(57) ABSTRACT

A three-dimensional reference image is displayed along with an ultrasound image (tomogram). The three-dimensional reference image has a first existing line representing a first puncture needle and a second prospective line indicating the prospective puncture path of a second puncture needle. The position and orientation of the probe are adjusted by the user with reference to the three-dimensional reference image so that the second prospective line has an appropriate position relative to the first existing line. After the adjustment, the second puncture needle is inserted into the body using a puncture adaptor provided on the probe. A second existing line is displayed in the three-dimensional reference image when the insertion of the second puncture needle is completed.

11 Claims, 18 Drawing Sheets

(51) Int. Cl.
    *A61B 8/14* (2006.01)
    *A61B 18/14* (2006.01)
    *A61B 18/00* (2006.01)

(52) U.S. Cl.
    CPC ............... *A61B 18/1477* (2013.01); *A61B 2018/00595* (2013.01)

(56) References Cited

U.S. PATENT DOCUMENTS

| | | |
|---|---|---|
| 2005/0033160 A1 | 2/2005 | Yamagata et al. |
| 2005/0090742 A1 | 4/2005 | Mine et al. |
| 2007/0010743 A1 | 1/2007 | Arai |
| 2012/0179040 A1 | 7/2012 | Arai et al. |
| 2012/0184851 A1 | 7/2012 | Arai et al. |
| 2012/0184852 A1 | 7/2012 | Arai et al. |
| 2013/0197357 A1 | 8/2013 | Green et al. |

FOREIGN PATENT DOCUMENTS

| | | |
|---|---|---|
| JP | 2007236767 A | 9/2007 |
| JP | 2008061858 A | 3/2008 |
| JP | 2011050625 A | 3/2011 |
| JP | 2012135394 A | 7/2012 |
| JP | 2013240369 A | 12/2013 |
| WO | 9823214 A1 | 6/1998 |
| WO | 9823214 A1 | 6/1998 |
| WO | 2004098414 A1 | 11/2004 |
| WO | 2010125505 A1 | 11/2010 |
| WO | 2014002066 A2 | 1/2014 |

OTHER PUBLICATIONS

Extended European Search report for European Application No. 15803684, dated Mar. 13, 2018, 6 pages.

International Search Report dated Aug. 4, 2015 for International Patent Application No. PCT/JP2015/063497.

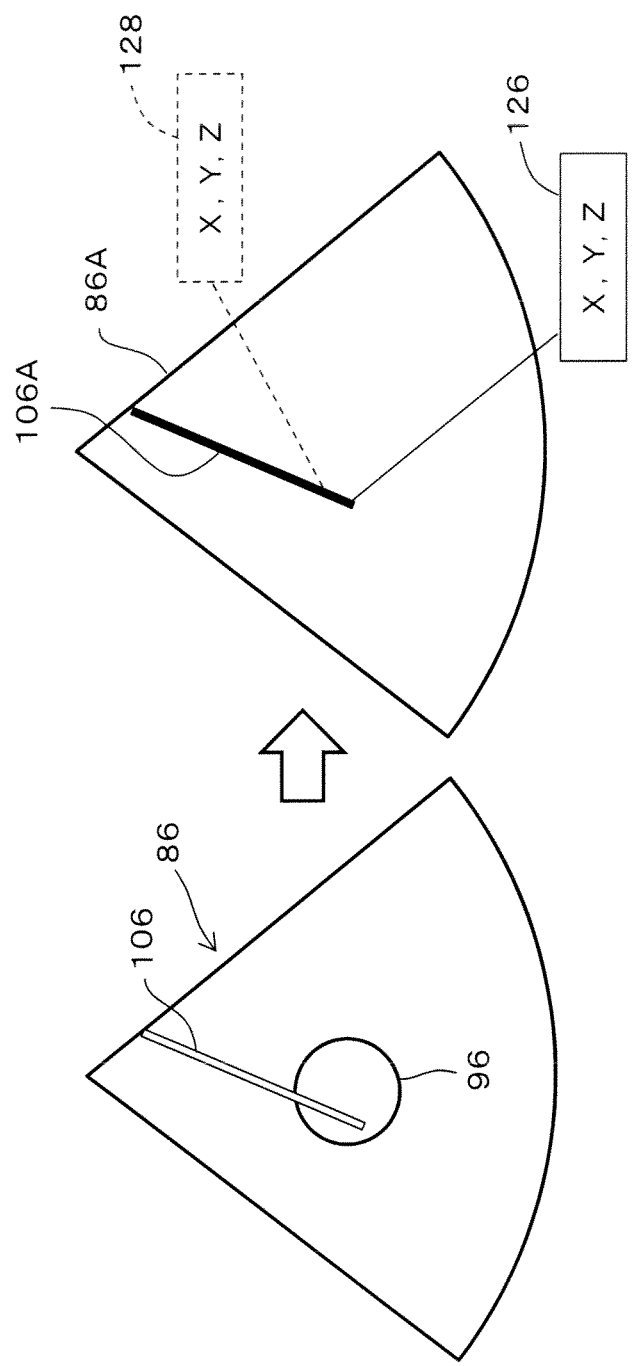

MEDICAL TREATMENT SYSTEM

CROSS-REFERENCE TO RELATED APPLICATIONS

This application is a national phase claiming the benefit of and priority to International Patent Application No. PCT/JP2015/063497, entitled "MEDICAL TREATMENT SYSTEM", filed May 11, 2015, which claims priority to Japanese Patent Application No. 2014-115453, entitled "MEDICAL TREATMENT SYSTEM", filed Jun. 4, 2014, which are hereby incorporated by reference in their entireties.

TECHNICAL FIELD

The present disclosure relates to medical systems, in particular to techniques to assist insertion of two or more puncture needles.

BACKGROUND

Ultrasonic diagnostic systems are widely used in medical fields as medical systems. Ultrasonic diagnostic systems are used in surgeries and treatments. For example, an ultrasonic diagnostic system is used to safely insert a puncture needle into a living body in order to retrieve tissues, inject medicine, treat tissues, or for other purposes. Specifically, a puncture adapter (attachment tool) is attached to a probe, and a puncture needle is set on the puncture adapter. A user inserts the puncture needle supported by the puncture adapter into a living body while viewing ultrasonic images. The puncture adapter is generally used to guide a puncture needle such that an insertion path is within a beam scan plane. A user inserts a puncture needle while viewing a target image (for example, a tumor image) and a puncture needle image in ultrasonic images. For example, insertion of a puncture needle is stopped when a tip of the puncture needle or its electrode portion reaches the center of a target such that a certain treatment can be performed under that condition.

In recent years, high-frequency medical treatments using two or more puncture needles have been started to be actually used. For example, two or more tips of puncture needles are positioned in a surrounding or vicinity area of a target such that high-frequency signals are supplied to electrode portions on the tips. In this way, medical treatment to cauterize a target is performed. As a puncture needle for such medical treatment, a bipolar-type treatment tool with a pair of electrodes is known. Positioning two or more puncture needles, for example, in parallel to each other with the tips aligned to each other in a living body is not an easy task. Realization of a system to assist such an operation is strongly desired.

It should be noted that, as a navigation technique or diagnostic assistant technique, techniques to display one or more reference images with an ultrasonic image (generally, a two-dimensional sectional image) are known (for example, Patent Literature 1). In those techniques, volume data obtained by an X-ray CT apparatus, an MRI apparatus, a three-dimensional ultrasonic diagnostic apparatus, or any other apparatuses are used. Based on the obtained volume data, images such as a three-dimensional image representing a three-dimensional space including the beam scan plane and a two-dimensional reference image representing the cross section corresponding to the beam scan plane are generated and displayed. In such a case, when a probe is moved, the ultrasonic images also change in accordance with the position and the orientation of the probe. The three-dimensional reference images and the two-dimensional reference images also change accordingly.

CITATION LIST

Patent Literature

Patent Literature 1: WO 2004/098414
Patent Literature 2: JP 2007-236767 A
Patent Literature 3: JP 2011-50625 A
Patent Literature 4: JP 2008-61858 A
Patent Literature 5: JP 2013-240369 A
Patent Literature 6: US 2013/0197357 A
Patent Literature 7: JP 2006-326128 A

SUMMARY

Technical Problem

There is a need for realization of a system which can assist an insertion operation of two or more puncture needles, in particular, insertion of the puncture needles while accurately arranging the relative relationships between the puncture needles. Although Patent Literatures 2, 3, 4, and 5 disclose systems which assist insertion of a puncture needle, these system do not assist insertion of two or more puncture needles.

Patent Literature 6 discloses a system for assisting insertion of two or more puncture needles. This system virtually reproduces a state of a real space as a three-dimensional image. For example, the three-dimensional image shown in FIG. 14B in Patent Literature 6 includes a drawing showing the center of a target and its condition, a virtual image depicting a puncture tool which is inserted first, another virtual image depicting a puncture tool which is inserted second (inserted halfway), and an image of an ultrasonic cross section. In order to form such three-dimensional images, position information is obtained for the probe and each of puncture tools.

However, in the system disclosed in Patent Literature 6, respective puncture tools and the ultrasonic probe are handled completely independently. Specifically, the probe is required to be positioned independently relative to a target. In addition, respective puncture tools should be accurately positioned relative to the target individually.

A three-dimensional image disclosed in Patent Literature 6 includes an indicator showing a trajectory of a puncture tool which is to be inserted second. Although the timing at which the indicator appears in the three-dimensional image is unclear, it can be assumed that the indicator showing the trajectory does not appear in the three-dimensional image until the puncture tool is actually inserted inside a living body, or the puncture tool is oriented to be inserted outside a body. Therefore, it is impossible to spatially determine the second insertion path (prospective insertion path) relative to the first insertion path (existing insertion path) by a probe operation alone before starting the use of the second treatment tool after insertion of the first treatment tool.

Patent Literature 7 discloses a medical system which displays a treatment area of a puncture tool in an image. However, this system does not support insertion of two or more puncture needles.

An object of the present disclosure is to assist insertion of two or more puncture needles. Another object is to enable an appropriate and easy setting of an insertion path of a puncture needle for subsequent insertion relative to a puncture needle after insertion completion. Yet another object is to enable a correct setting of an insertion path of a puncture needle for subsequent insertion relative to a puncture needle after insertion completion without requiring the puncture needle to be set in a puncture adapter.

Solution to Problem

A medical system according to an embodiment of the present disclosure includes a probe that includes a puncture adapter which sequentially guides two or more puncture needles to be inserted into a three-dimensional space in a living body. The probe outputs reception signals by transmitting and receiving ultrasonic waves to and from the three-dimensional space. The medical system further includes a calculator that calculates a prospective insertion path based on position information obtained for the probe. The medical system further includes an ultrasonic image generator that generates an ultrasonic image based on the reception signals. The medical system further includes a register that registers an existing insertion path based on at least one of the position information of the puncture needle at the time of insertion completion and the prospective insertion path. The medical system further includes a three-dimensional reference image generator that includes a unit for forming a three-dimensional reference image based on volume data obtained from the three-dimensional space. The three-dimensional reference image generator generates a three-dimensional reference image that includes the three-dimensional ultrasonic image, a three dimensional existing insertion path symbol representing the existing insertion path of the puncture needle after insertion completion, and a three-dimensional prospective insertion path symbol representing the prospective insertion path of the puncture needle for subsequent insertion.

According to the above configuration, the existing insertion path symbol and the prospective insertion path symbol are displayed in the three-dimensional reference image. When the position and the orientation of the probe are changed, the position and the orientation of the prospective insertion path symbol also change accordingly in the three-dimensional reference image. A user adjusts the position and the orientation of the probe such that the prospective insertion path symbol is appropriately positioned relative to the existing insertion path symbol. To determine the prospective insertion path of the second or later puncture needle, the future insertion path of the puncture needle can be appropriately set by merely adjusting the position and the orientation of the probe without requiring the puncture needle to be set in the puncture adapter. Because the insertion path of the puncture needle after insertion completion is displayed as the existing insertion path symbol, the insertion can be simulated by referring to the existing insertion path symbol of the puncture needle after insertion completion together with the prospective insertion path symbol. Once the insertion is started, it becomes generally impossible to freely change the orientation of the tip of the puncture needle (actual insertion direction). Therefore, a safe insertion can be performed by optimizing the prospective insertion path before the actual insertion by referring to the three-dimensional reference image. The existing insertion path may also be referred to as an "actual insertion path."

Although the puncture needle is preferably a puncture tool for treatment, the puncture needle may be a general puncture needle or others. It is preferable that after completion of the first insertion, the first puncture needle is released from the puncture adapter such that the position and the orientation of the probe can be adjusted under such condition. The position information of the probe is obtained by, for example, a sensor provided for the probe. A sensor may be provided for the puncture adapter or the puncture needle. A sensor provided for the probe and a sensor provided for the puncture needle may both be used. The positional relationship between the probe and the puncture adapter is typically fixed and known. When the positional relationship is variable, it is preferable to dispose a sensor or the like to sense the positional relationship between the two. The prospective insertion path is calculated as, for example, coordinate information within the three-dimensional space or the scan plane. A register registers an existing insertion path upon completion of the insertion. For example, a prospective insertion path at the time of insertion completion becomes an existing insertion path. In that case, the amount of insertion, the tip position, and other information may be registered. The timing of completion of existing insertion may be determined by a certain input from a user or automatically when the tip of the puncture needle reaches a certain depth. The volume data reside in an internal memory, an external storage medium, or on a network. It is preferable to use the most recent volume data available. Respective symbols are a graphic, an indicator, display element, diagram, and others. Each symbol may indicate a direction alone, a direction plus depth (target point), or others. Each symbol may also indicate an electrode array. It is preferable that each symbol is identifiably displayed in a unique combination of color, brightness, shape, and line type such that each symbol is distinguishable.

When the position and the orientation of the probe are changed in an adjustment process after completion of the previous insertion and before start of the next insertion, the position and the orientation of the prospective insertion path symbol may be changed while maintaining the position and the orientation of the existing insertion path symbol in the three-dimensional reference image. The next insertion using the puncture adapter may be performed after completion of the adjustment of the position and the orientation of the probe.

Specifically, the existing insertion path symbol and the prospective insertion path symbol in the three-dimensional image are referred to in the adjustment process. In the three-dimensional image, the existing insertion path symbol does not move unless the view point or the like is changed. In contrast, the position and the orientation of the prospective insertion path symbol changes in accordance with adjustment of the position and the orientation of the probe. For example, in order to appropriately treat a target, the position and the orientation of the probe are adjusted such that the prospective insertion path symbol is spaced from the existing insertion path symbol for an appropriate distance and the two symbols are positioned in parallel.

The probe may form a beam scan plane traversing the three-dimensional space. The three-dimensional reference image may include a scan plane symbol representing the beam scan plane. The prospective insertion path symbol may be displayed within the scan plane symbol in the three-dimensional reference image.

Because the scan plane symbol is displayed in the three-dimensional image according to the above configuration, the position and the orientation of the probe can be adjusted by referring to the scan plane symbol. The scan plane symbol may pass through the target, and the position and the orientation of the probe may be adjusted such that the prospective insertion path is appropriately positioned relative to the target and the existing insertion path. Once the adjustment of the position and the orientation of the probe has been completed, insertion can be subsequently performed while maintaining that condition. In other words, after completion of the adjustment of the position and the orientation of the probe, another, later adjustment of the position and the orientation of the puncture needle is basically unnecessary.

The three-dimensional reference image may further include a target symbol that corresponds to or includes the target image. For example, when a target tissue is unclearly displayed in the three-dimensional image, the puncture target can be clearly recognized by displaying the target symbol. When a puncture is desired in an area surrounding the target, a target symbol which is sufficiently larger than the target may be displayed. Each insertion path can be set more easily by using the target symbol as a reference.

An orthogonal sectional image generator may be provided for generating an orthogonal sectional image representing a cross section orthogonal to the prospective insertion path. The orthogonal sectional image may include a position mark representing the existing insertion path and another position mark representing the prospective insertion path. Because an image having an insertion direction as a viewing direction can be obtained in accordance with this configuration, the distance between the insertion paths and their arrangement can be easily recognized. The orthogonal sectional image may be a cross section image or a projected image. A target or a target symbol may be displayed in such an image.

A sensor that senses information usable to determine an amount of insertion of a puncture needle for subsequent insertion may be provided. A position of the orthogonal cross section on the prospective insertion path may be changed according to the information sensed by the sensor. According to this configuration, the orthogonal sectional image changes in accordance with a movement of the puncture needle. A sensor which can obtain position information may be used as the sensor.

The ultrasonic image may be a two-dimensional sectional image representing a beam scan plane formed by the probe. The two-dimensional sectional image may display a prospective insertion path symbol representing the prospective insertion path. When the puncture needle after insertion completion is in a vicinity space of the beam scan plane, the two-dimensional sectional image displays an existing insertion path symbol representing the existing insertion path of the puncture needle in addition to the prospective insertion path symbol. The vicinity space is, for example, a space that expands in a thickness direction with the beam scan plane at the center. The thickness of the vicinity space may be defined to be equal to the width of the ultrasonic beam.

As the ultrasonic image, a two-dimensional sectional image including at least a prospective insertion path symbol may be displayed. The ultrasonic image may further display the existing insertion path symbol and others. The register may register the existing insertion path based on information entered by a user who has referred to a puncture needle image in the ultrasonic image. The register may register the existing insertion path based on signals from a sensor disposed to each of the puncture needles. The puncture needles may be high-frequency treatment tools. High-frequency signals may be supplied to an electrode array of the puncture needles inserted in the three-dimensional space. A unit may be further provided for displaying, in the three-dimensional image, a treatment area symbol representing a treatment area of the two or more puncture needles.

Advantageous Effects of Invention

The present invention assists insertion of two or more puncture needles. Alternatively, the present invention facilitates accurate positioning of a puncture needle for subsequent insertion relative to a puncture needle after insertion completion. Alternatively, the present invention realizes an appropriate insertion path relative to the insertion path of a puncture needle after insertion completion without requiring the puncture needle to be set in a puncture adapter.

BRIEF DESCRIPTION OF DRAWINGS

FIG. 10 is a diagram showing a third registration example of an existing insertion path;

DESCRIPTION OF EMBODIMENTS

Figure 1:
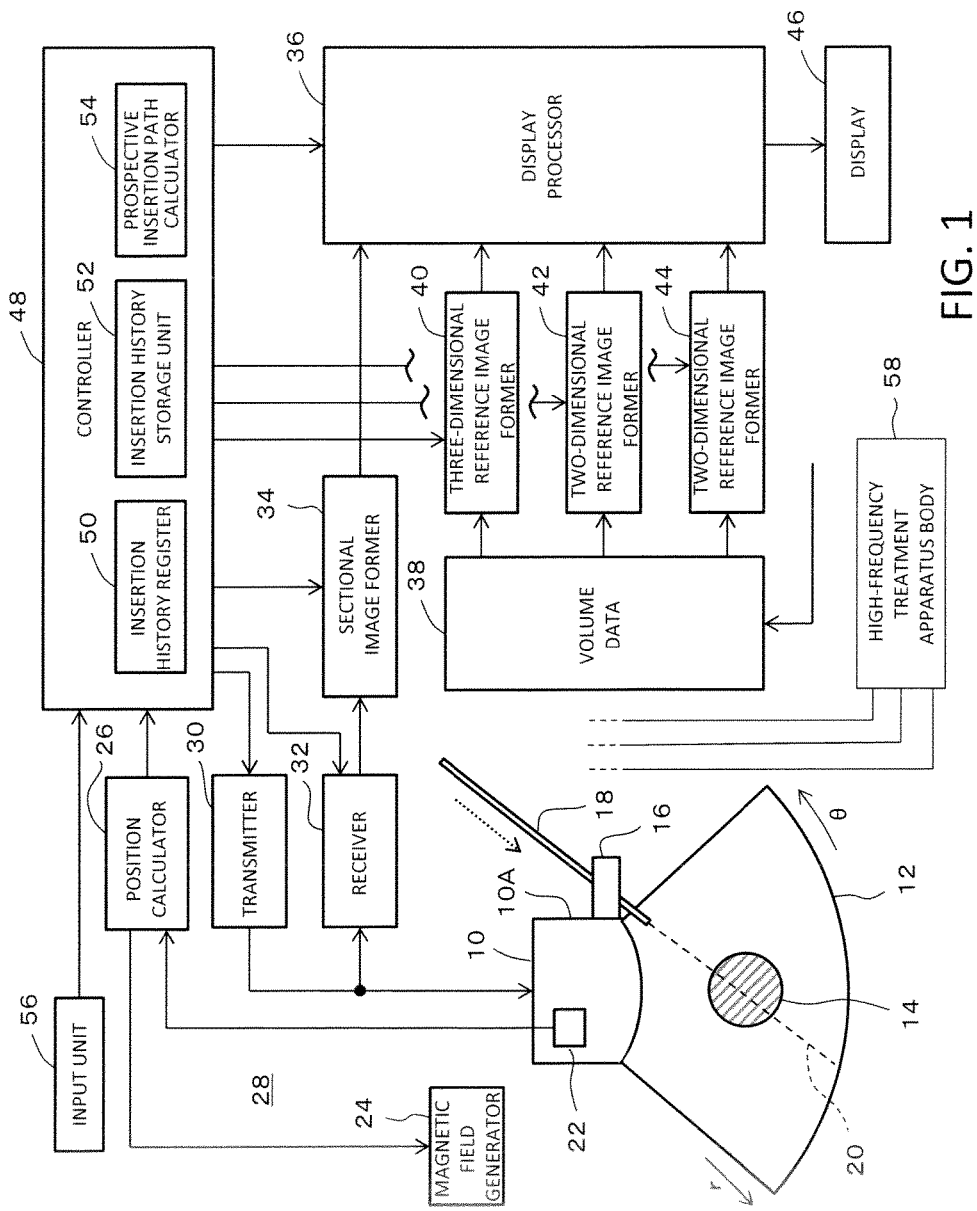
FIG. 1 is a block diagram showing a first embodiment of an ultrasonic diagnostic system according to the present disclosure.

FIG. 1 is a block diagram showing a first embodiment of an ultrasonic diagnostic system as a medical system according to the present disclosure. This ultrasonic diagnostic system can assist insertion of two or more puncture needles.

In FIG. 1, a probe 10 is an ultrasonic transceiver which is used in contact with a surface of a living body in this embodiment. The probe 10 is connected to the body of an ultrasonic diagnostic system via a probe cable (not shown). The probe 10 includes a 1D transducer array which is formed by two or more transducer elements. It is of course possible to use a 2D transducer array. The transducer array forms ultrasonic beams. A scan plane 12 is formed by an electronic scan with the ultrasonic beams. The scan plane 12 is a two-dimensional data retrieved area.

In FIG. 1, "r" represents the depth direction, in other words, the beam direction, and "θ" represents the electronic scan direction. Well-known electronic scan methods include an electronic linear scan method and an electronic sector scan method.

A target cross section 14 has appeared on the scan plane 12. The probe 10 includes a probe body 10A which is held by a user (such as a medical practitioner or a medical technologist). A puncture adapter 16 is detachably attached to the probe body 10A. The puncture adapter 16 is mounting hardware which guides a puncture needle 18 at a certain distance and angle relative to the probe body 10A. In FIG. 1, the insertion direction, in other words, the insertion path, is represented by a reference numeral 20. In FIG. 1, the insertion path 20 passes through the target cross section 14. The puncture needle 18 is supported by the puncture adapter 16 such that the actual insertion path is within the scan plane 12, in other words, the puncture needle advances on the scan plane 12. The puncture adapter 16 may include a sensor which senses the amount of insertion. The puncture adapter 16 may also include a mechanism to change the insertion angle and the puncture needle supported position. In that case, a sensor may sense the insertion angle and the puncture needle supported position. In the example shown in the drawing, the positional relationship between the probe 10 and the insertion path 20 is always constant. As described below, a sensor may be disposed on the puncture needle 18 itself to sense the positional relationship.

The probe 10 includes a magnetic sensor 22. This magnetic sensor 22 senses the position and the orientation of the probe 10 in a three-dimensional space. A magnetic field generator 24 disposed in a three-dimensional space functions to generate an X-axis magnetic field, a Y-axis magnetic field, and a Z-axis magnetic field. The magnetic sensor 22 senses the position of the probe 10 in each axis direction and a rotation angle of the probe 10 about each axis by detecting these magnetic fields. Specifically, a position calculator 26 calculates the position information indicating the position and the orientation of the probe 10 based on output signals from the magnetic sensor 22. The position calculator 26 also functions as a controller of the magnetic field generator 24. A locating system 28 is formed by the magnetic sensor 22, the magnetic field generator 24, and the position calculator 26. As the locating method, an optical method, an electromagnetic wave method, and other methods can be raised in addition to the magnetic field method.

A transmitter 30 is a transmission beam former. The transmitter 30 supplies transmission signals in a parallel manner to the transducer array. This causes the transducer array to form transmission beams. During receiving, reflected waves from the living body are received by the transducer array. Then, reception signals are sent from transducer elements to a receiver 32. The receiver 32 is a reception beam former. The receiver 32 forms beam data which correspond to reception beams by applying a phasing addition process to the reception signals. The beam data are transmitted to a sectional image former 34 via a signal processing module (not shown).

The sectional image former 34 sequentially receives receive frame data. A single receive frame datum is formed by beam data sets which are arranged in line in the electronic scan direction. Each of the beam data sets is formed by echo data sets which are arranged in line in the depth direction.

The sectional image former 34 is a module which forms real time sectional images as B mode images (two-dimensional ultrasonic images) based on the reception frame data. The sectional image former 34 includes a digital scan converter. Further, in the present embodiment, the sectional image former 34 functions to synthesize a graphic image on a sectional image. Image data of such a sectional image (synthesized image) are transmitted to a display processor 36. The generation and synthesization of graphic data may be performed by the display processor 36 or a controller 48.

A memory 38 stores volume data. The volume data are obtained from a three-dimensional space in a living body by, for example, an X-ray CT apparatus, an MRI apparatus, an ultrasonic diagnostic apparatus, and other apparatuses. In the present embodiment, the volume data are stored in the internal memory 38. However, the volume data may be stored in an external storage medium, in a file server on a network, or any other media.

The scan plane 12 corresponds to a cross section in a three-dimensional space, which corresponds to the volume data. In other words, the volume data corresponding to the three-dimensional space which includes a movement range of the scan plane 12 are stored in the memory 38.

A three-dimensional reference image former 40 is a module which forms a three-dimensional image depicting the inside of a living body based on the volume data. The three-dimensional reference image includes an image such as a volume rendering image and a surface rendering image. As an example of the three-dimensional reference image, an ultrasonic image, a CT image, and an MRI image can be raised. The three-dimensional reference image of the present embodiment includes a three-dimensional graphic image. Graphics may be synthesized by the display processor 36 or any other unit. The graphic image included in the three-dimensional reference image is updated in real time based on the position information of the probe 10. For example, the three-dimensional reference image former 40 includes a symbol indicating an insertion path such that the position and the orientation of the symbol are updated in real time in accordance with a movement of the probe 10. The image data of the three-dimensional reference images are transmitted to the display processor 36.

A two-dimensional reference image former 42 is a module which forms a corresponding sectional image as a first two-dimensional reference image based on the volume data. Specifically, the sectional data corresponding to the scan plane 12 are extracted from the volume data, and a sectional image is formed based on the extracted data. The formed sectional image is the corresponding sectional image. The two-dimensional reference image former 42 also functions to synthesize a graphic image to the corresponding sectional image. This function may be performed by the display processor 36 or any other unit.

Another two-dimensional reference image former 44 functions to form an orthogonal sectional image as a second reference image. Specifically, the sectional data corresponding to a cross section of an insertion path which is cut at a predetermined depth is extracted and a sectional image is formed based on the extracted data. The formed sectional image is the orthogonal sectional image. The two-dimensional reference image former 44 functions to synthesize a graphic image to the orthogonal sectional image. This function may be performed by the display processor 36 or any other unit. The image data of the orthogonal sectional image are transmitted to the display processor 36. A reference image former other than the reference image formers 40, 42, 44 shown in FIG. 1 may also be disposed. When a 3D probe is used as the probe 10 to obtain the volume data, each reference image may be formed based on the volume data.

The display processor 36 functions to synthesize two or more input image data sets to generate display screen data. The generated display screen data are transmitted to a display 46. In the present embodiment, the display 46 displays a real-time sectional image, a three-dimensional reference image, a corresponding sectional image, and an orthogonal sectional image. The images other than the real-time sectional image are reference images, which are also updated in real time. However, as the volume data have been obtained for the same target in advance, the real-time sectional image is the only image which displays the current condition of the target. The real-time sectional image is also the only image in which the puncture needle actually appears.

In the present embodiment, a high-frequency treatment apparatus body 58 supplies high-frequency signals to two or more puncture needle treatment tools. The high-frequency treatment apparatus body 58 has functions including selecting an electrode set to be actually used from two or more electrodes of the two or more puncture needle treatment tools and cooling the two or more puncture needle treatment tools.

Each unit (each block) shown in FIG. 1 is basically configured by one or more processors, chips, circuits, and other elements, except for some of the units such as the probe and the puncture needle. Each chip, processor, and circuit may correspond to two or more units. Each unit may be realized by a software function. Such software may be executed by a CPU. A single processor may execute all the software functions, or two or more processors may execute the software functions.

The controller 48 is configured with a CPU and a program. The controller 48 controls each unit (each block) shown in FIG. 1. The controller 48 includes an insertion history register 50, an insertion history storage unit 52, and a prospective insertion path calculator 54. In a process of insertion of two or more puncture needles, when the insertion of each puncture needle is completed, the insertion history register 50 registers in the memory the insertion path or position information of each puncture needle as an insertion actual record (insertion history). For example, when it is determined that the insertion of a puncture needle is completed, the prospective insertion path at that time is registered as an existing insertion path. The existing insertion path is registered for each of the puncture needles. The insertion history storage unit 52 is a storage area in which the information registered by the insertion history register 50 is stored. The register timing can be manually set or automatically designated. When the treatment is completed, the stored information is deleted from the insertion history storage unit 52. Such information may be separately stored. Coordinate information of the existing insertion path or the position information of the probe representing the coordinate information may be registered. The insertion history storage unit 52 may also register the amount of insertion, that is, the depth of insertion. If registered, such information can be used to show an actual depth by a length of an existing insertion path symbol when displaying the symbol.

The prospective insertion path calculator 54 is a module which calculates an insertion path 20 of the puncture needle 18 which is to be guided by the puncture adapter 16 (in other words, the prospective insertion path) based on the position information output from the position calculator 26. For example, coordinate information of the prospective insertion path on the scan plane and/or the coordinate information of the prospective insertion path in a three-dimensional space is calculated. In either case, information to directly or indirectly determine the prospective insertion path in a three-dimensional space is calculated. The calculated information is transmitted to the three-dimensional reference image former 40, the two-dimensional reference image former 42, and the two-dimensional reference image former 44, as required. The information registered in the insertion history storage unit 52 is also transmitted to these reference image formers 40, 42, 44.

The input unit 56 is formed by, for example, an operation panel. The input unit 56 includes an input device such as a switch and a trackball. Although the position information is measured by a magnetic field method in the present embodiment, the position information may be measured by other methods such as an optical measurement and a measurement using radio waves as described above. Further, a device such as an acceleration sensor may be used.

Each of the above-described units and their operations are described further in detail below.

Figure 2:
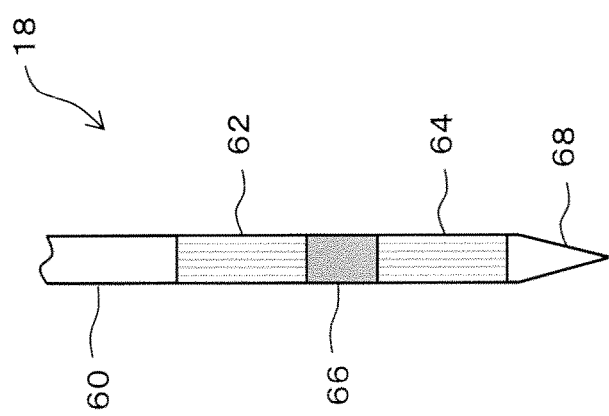
FIG. 2 is a diagram showing an example of a puncture needle for medical treatment.

FIG. 2 shows an example of a puncture needle. The depicted puncture needle 18 is a tool to perform high-frequency treatment. FIG. 2 shows an enlarged view of the tip of the puncture needle 18. The puncture needle 18 is a bipolar-type high-frequency treatment tool. Specifically, the puncture needle 18 includes an insulator 66, and two electrodes 62, 64 which sandwich the insulator 66. Reference numeral 60 represents a shaft body. Reference numeral 68 represents a tip having a tapered shape. A treatment tool having another structure may, of course, be used. In the present embodiment, two or three puncture needles are used simultaneously during treatment to apply a high-frequency cauterization treatment to a target (the target tissue to be treated).

Figure 3:
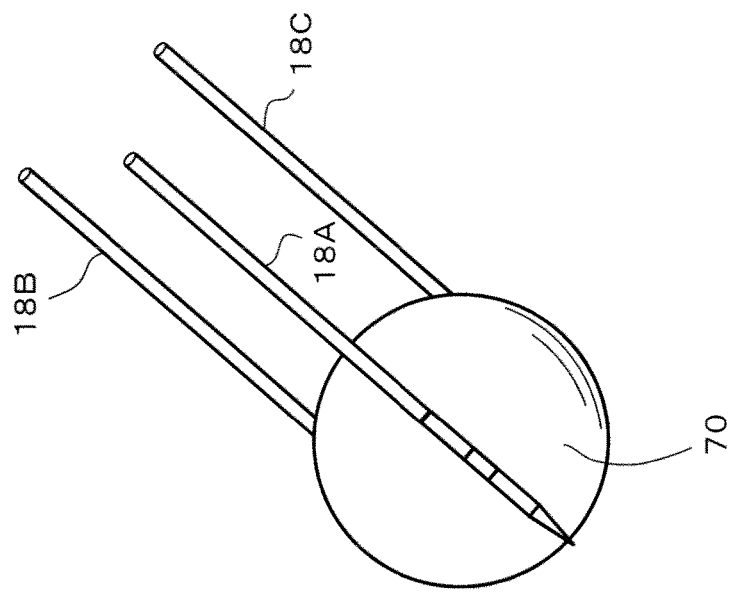
FIG. 3 is a diagram showing a view in which insertion of more than one puncture needle is performed.

FIG. 3 shows a puncture needle array. Specifically, the drawing shows a view in which three puncture needles (treatment tools) 18A, 18B, 18C are used to treat a target 70. In the depicted example, the three puncture needles 18A, 18B, 18C are arranged such that the target 70 is surrounded by the tips of the three puncture needles 18A, 18B, 18C (in other words, the three puncture needles 18A, 18B, 18C are positioned around the target 70). Under such conditions, all or some of the electrodes are selected and high-frequency signals are supplied to the selected electrodes. In this way, a cauterization treatment is applied to the target 70.

In achieving the above-described arrangement, the three puncture needles 18A, 18B, 18C are inserted to be in parallel to each other and arranged such that the tips are aligned (equal amounts of insertion). The three puncture needles 18A, 18B, 18C are arranged with equal intervals therebetween in the depicted example. Therefore, an equilateral triangle is formed, when viewed from the insertion direction. Various arrangements are selectable in accordance with the shapes of the target 70 or other conditions.

It should be noted that the treatment may be performed with two puncture needles. In the description below, it is assumed that two puncture needles are used to treat a target.

Figure 4:
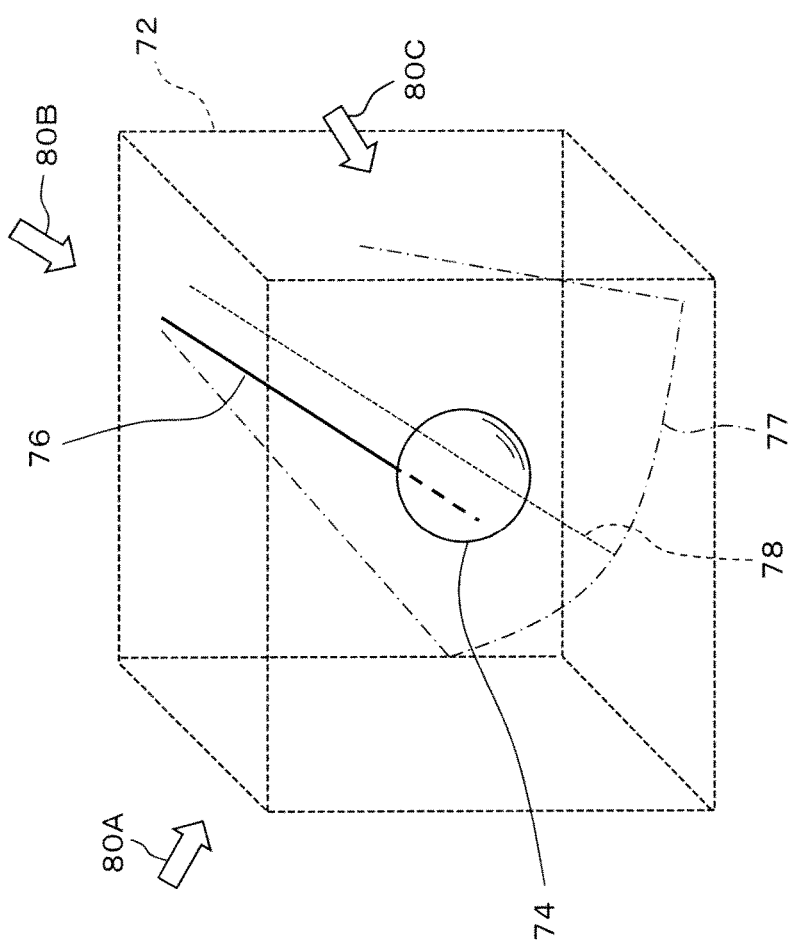
FIG. 4 is a diagram showing an example of a three-dimensional reference image.

FIG. 4 shows a three-dimensional reference image 72. The three-dimensional reference image 72 may also be referred to as a "body mark." The three-dimensional reference image 72 represents a three-dimensional space inside a living body as a three-dimensional image. As the representing method, a volume rendering method, a surface rendering method, and other methods can be raised. The three-dimensional reference image 72 includes a target (target image) 74 which is a tumor or the like. The three-dimensional reference image 72 further includes a first existing line (first existing insertion path symbol) 76, a second prospective line (second prospective insertion path symbol) 78, and a scan plane mark (scan plane symbol) 77. The first existing line 76 is generated based on the existing insertion path which has been registered when the first insertion is completed. The second prospective line 78 is a line within a scan plane mark 77. The second prospective line 78 represents a prospective insertion path of a puncture needle for subsequent insertion. Before an actual second insertion, the second insertion path can be recognized by referring to the second prospective line 78 while recognizing the first insertion path by referring to the first existing line 76. When the direction or the orientation of the probe on a body surface is changed, the scan plane mark 77 and the second prospective line 78 also move accordingly. A user can set the position and the orientation of the probe such that the second prospective line 78 is appropriately positioned relative to the first existing line 76. On this occasion, because the scan plane mark 77 is displayed together with the second prospective line 78, the user can intuitively and easily recognize the orientation or other conditions of the probe.

In addition to the target image 74, another tissue may be displayed in the three-dimensional reference image 72. In that case, a blood vessel image may also be displayed to ensure safety. Blood vessels may be displayed using Doppler information obtained in the three-dimensional space. Further, by defining a vicinity space around the scan plane mark 77 such that the vicinity space has a certain thickness in the thickness direction of the scan plane mark 77 positioned at the center, the first existing line 76 may be highlighted or otherwise indicated when the first existing line 76 is within the vicinity space. In this way, the existing insertion path and a future insertion path can be easily displayed together on the same scan plane.

In forming the three-dimensional reference image 72, rendering origins (that is, a view point) may be set in various directions. Examples of the rendering origin are shown by reference numerals 80A, 80B, 80C. For example, the view direction may be defined along the insertion path as depicted by reference numeral 80B.

Figure 5:
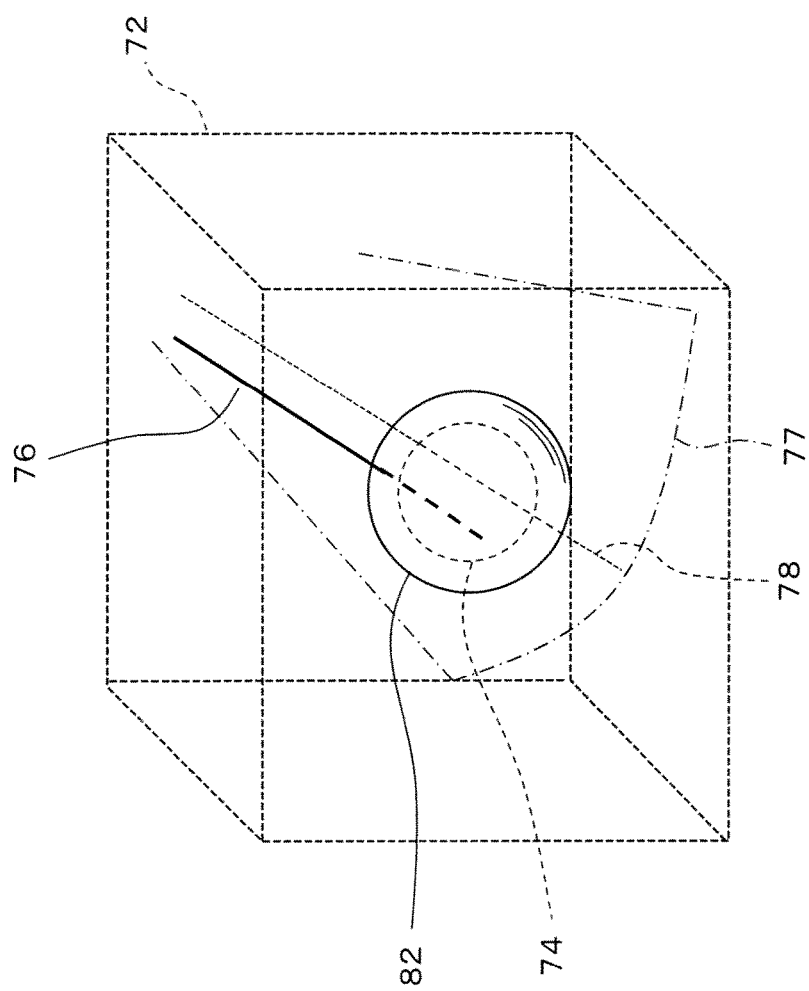
FIG. 5 is a diagram showing a guide ball as a target symbol.

FIG. 5 shows the three-dimensional reference image 72 shown in FIG. 4. In FIG. 5, the elements similar to those shown in FIG. 4 are represented by identical reference numerals. The description of these elements is omitted. The same applies to each of the drawings described below.

In FIG. 5, the three-dimensional reference image 72 includes a guide ball 82 as a target guide. The guide ball 82 may be a sphere which is equal to the target image 74 in size or a sphere formed around the target image 74. The target image 74 is actually a graphic image. For example, when the target image 74 is unclear in the three-dimensional reference image 72, the guide ball 82 which is equal in size to the target may be displayed to clarify the boundaries and appearance. Alternatively, when two or more puncture needles need to be positioned around the target image 74, the guide ball 82 which is larger than the target image 74 may be concentrically displayed in order to facilitate the recognition of the positional relationships between them. In this way, as shown in the drawing, the user can three-dimensionally and intuitively recognize that each insertion path passes through the guide ball 82. Therefore, the positional relationships among them can be easily understood. The size of the guide ball 82 or the size ratio of the guide ball 82 to the target image may be configured to be variable to any value by a user. Further, a set of multiple, concentric guide balls may be displayed.

In the volume data, the target may be automatically extracted so as to highlight the target or generate the guide ball based on the extracted target. The target automatic extraction process may alternatively be performed by a user by identifying the target in a sectional image or three-dimensional reference image.

Figure 6:
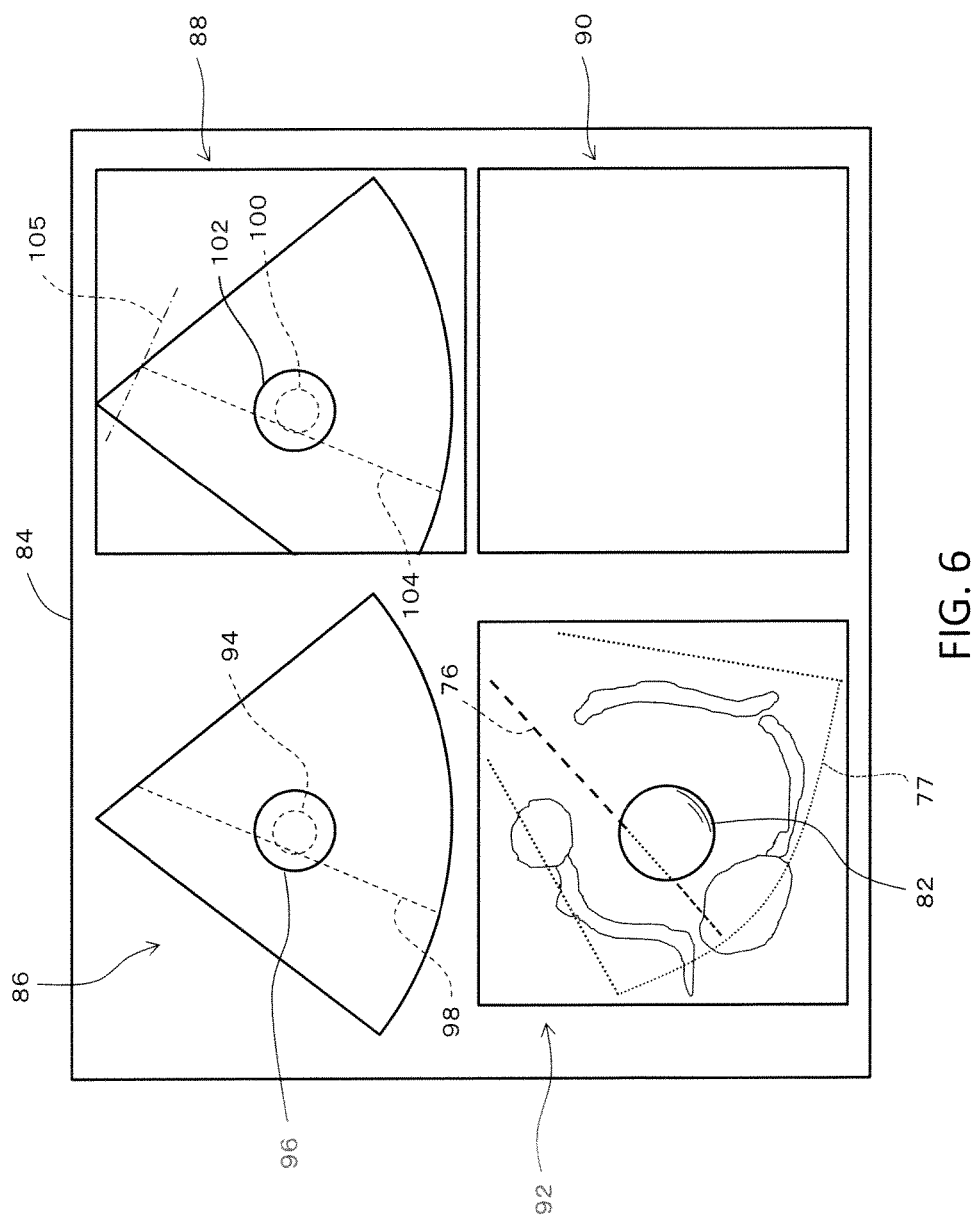
FIG. 6 is a diagram showing a display example before a first insertion.

FIG. 6 shows a display before the first insertion is performed. A screen 84 displays a sectional image (ultrasonic sectional image) 86, a corresponding sectional image 88 as a first two-dimensional reference image, an orthogonal sectional image 90 as a second two-dimensional reference image, and a three-dimensional reference image 92. It should be noted, however, that regarding the orthogonal sectional image 90, because the orthogonal cross section is not yet determined, the image display is not started.

The sectional image 86 is a real-time image generated by ultrasonic transmission/reception waves. In the sectional image 86, an insertion path is displayed as a first prospective line 98. The displayed insertion path is a graphic image. Because the positional relationship between the probe body and the puncture adapter is known as described above, the first prospective line 98 can be determined from the position information of the probe. In FIG. 6, the first prospective line 98 passes in the vicinity of a target 94 on one side. Reference numeral 96 represents a guide circle. The guide circle 96 represents a sectional image of the guide ball. Such an image may be displayed as required. A conventional sectional image 86 alone may be displayed.

The corresponding sectional image 88 is generated by retrieving surface data corresponding to the scan plane from the volume data. The volume data is obtained by, for example, a CT apparatus. In such a case, the corresponding sectional image 88 is a CT sectional image. A target 100 has appeared in the corresponding sectional image 88. A first prospective line 104 is displayed as a graphic or a symbol. Reference numeral 105 represents a line showing the position of a plane which is orthogonal to the first prospective line 104. The line 105 is positioned at the origin. The orthogonal sectional image corresponds to the line 105. It should be noted that the orthogonal sectional image is not displayed in the drawing because the amount of insertion is unknown at the time of the display.

The three-dimensional reference image 92 includes a first prospective line 76 representing a first insertion path, and a scan plane mark 77 including the first prospective line 76. The three-dimensional reference image 92 also includes the guide ball 82 as a three-dimensional sphere. The guide ball 82 surrounds the target. In this example, the insertion path is determined relative to not the target itself but the guide ball 82. However, as a result, the insertion path is determined relative to the target.

The position and the orientation of the probe are adjusted by the user while referring to each drawing in FIG. 6, in particular, the three-dimensional reference image 92, so as to arrange the insertion path to be at the right position and the orientation relative to the target or the guide ball 82. Specifically, in the three-dimensional reference image 92, the position and the orientation of the probe are adjusted such that the first insertion line 76 passes through the guide ball 82 at the right position and the angle. During the probe adjustment process, the sectional image 86 and the corresponding sectional image 88 are updated in real time. However, the positions of the first prospective lines 98, 104 are not variable in the images 86, 88.

Figure 7:
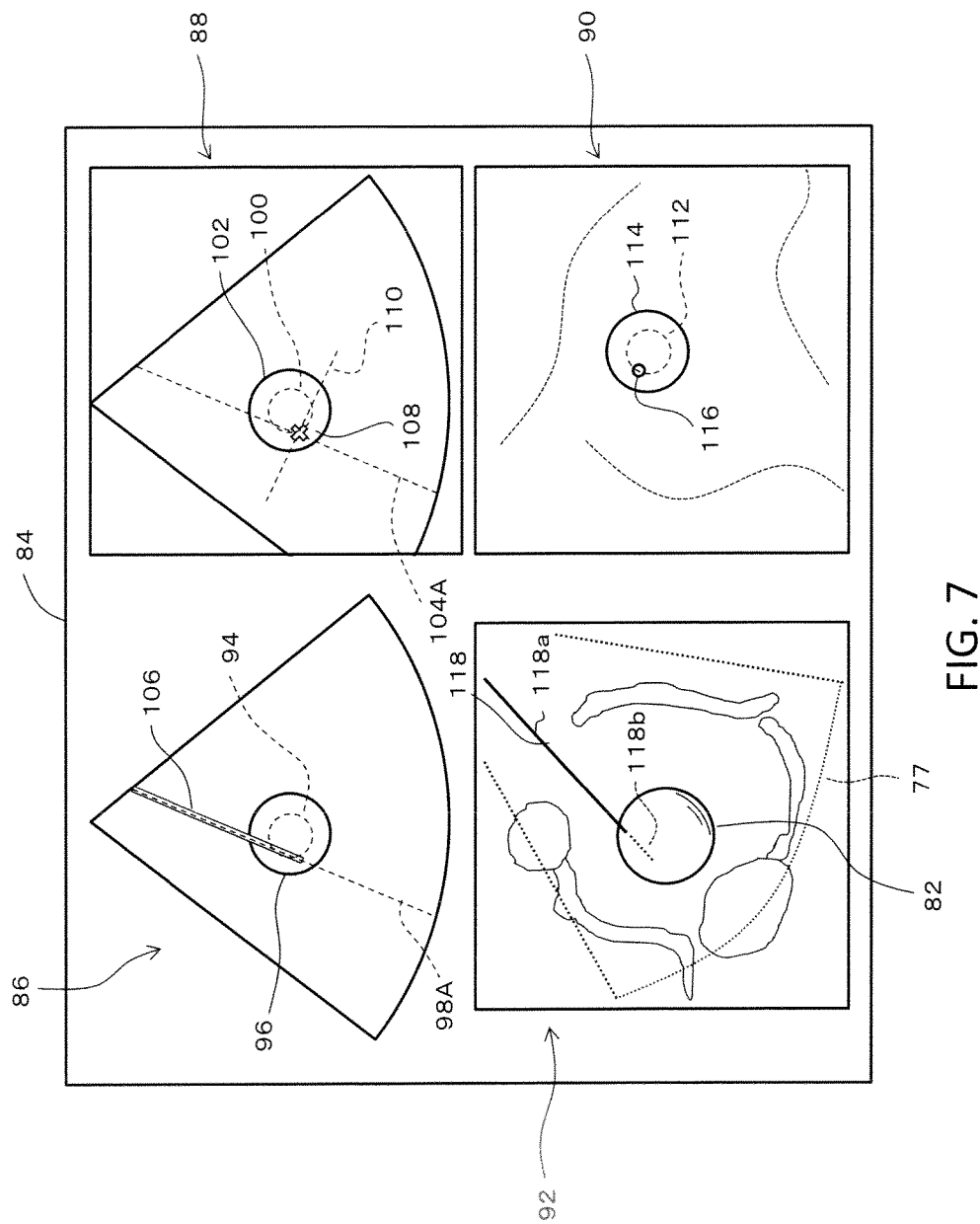
FIG. 7 is a diagram showing a display example when the first insertion is completed.

FIG. 7 shows a display example after completion of the first insertion. Specifically, the drawing shows the display after the insertion history registration has been completed for the first insertion.

A first needle image 106 has appeared in the sectional image 86. As the puncture needle is generally formed of a rigid member, echoes from the puncture needle are so strong that the inserted needle is displayed in the sectional image 86. Reference numeral 98A represents a first existing line. Upon completion of the insertion history registration of the first insertion, the first prospective line is replaced with the first existing line 98A. At the same time, a second prospective line is displayed. At the time of the generation of the prospective line, the second prospective line is displayed at the same position as the first existing line (therefore, no second prospective line is visible in FIG. 7). It should be noted that the two lines may be distinguishably displayed at that point. Alternatively, the display of the second prospective line may be delayed until the two lines are separately positioned. The first existing line 98A represents the insertion path fixed in the three-dimensional space. When the position and the orientation of the probe is changed relative to the three-dimensional space, the position and the orientation of the first existing line are changed, or the first existing line disappears from the sectional image 86. In contrast, the second prospective line moves unitedly with the probe in the three-dimensional space, whereas, in the sectional image 86, the second prospective line is unmovable similarly as the first prospective line described above. In other words, the second prospective line is constantly displayed at the same position. It may be understood in a manner that, upon the registration, the first prospective line is replaced with the second prospective line, and a new first existing line is independently generated. In either case, in the present embodiment, the first existing line and the second prospective line are generated from the first prospective line upon the registration (line separation process).

Also in the corresponding sectional image 88, upon completion of the insertion history registration of the first insertion, the first prospective line is replaced with the first existing line 104A. At the same time, a second prospective line is generated at the same position (not shown). In the corresponding sectional image 88, a mark 108 is displayed on the first existing line 104A. The mark 108 represents the tip of the puncture needle, an insulator, the center of the electrode, or other positions. In this example, the mark 108 represents the position of the tip of the puncture needle. The mark 108 moves or disappears with the first existing line 104A in accordance with a change in the position and the orientation of the probe. Reference numeral 110 represents an orthogonal line relative to the insertion path. The orthogonal sectional image 90 is the sectional image representing the orthogonal cross section identified by the orthogonal line. In the depicted example, a guide circle 114 is displayed as a graphic such that the guide circle 114 surrounds a target 112. Reference numeral 116 represents the position of the first existing line.

In the three-dimensional reference image 92, upon completion of the insertion history registration of the first insertion, the first prospective line is replaced with a first existing line 118. At the same time, a second prospective line is generated at the same position (not shown). The first existing line 118 is a fixed line in the three-dimensional space such that the first existing line 118 is not basically moved unless the view point or other conditions are changed. In contrast, the second prospective line moves together with the probe, that is, the scan plane mark 77. In the depicted example, a part of the first existing line 118 is inserted into the guide ball 82. Specifically, the first existing line 118 represents the line from the incident position into the three-dimensional space to the tip of the puncture needle in the three-dimensional space. The first existing line 118 consists of a portion 118b which is inside the guide ball 82 and the remaining portion 118a. As described above, each line is three-dimensionally depicted. Also in the three-dimensional reference image 92, the first existing line 118 and the second prospective line may be displayed at the same time distinguishably. Alternatively, the display of the second prospective line may be started after the second prospective line departs from the first existing line 118. Such display conditions may be configured to be freely customizable by users.

Figure 8:
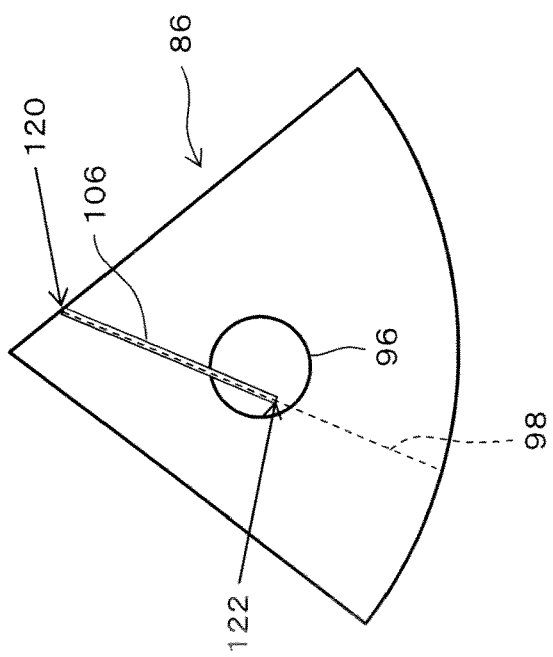
FIG. 8 is a diagram showing a first registration example of an existing insertion path.

FIG. 8 shows a first registration example of an insertion history. A sectional image 86 displays a guide circle 96 and a first prospective line 98. A first needle image 106 has appeared in the sectional image 86. As a first registration example, a user designates coordinates. Specifically, a user designates a tip position 122, and an incident position 120 into the sectional image 86 (in other words, the scan plane). Because the insertion path is known, the tip position 122 alone may be designated. Similarly as described above, upon this registration, the first existing line and the second prospective line are generated from the first prospective line.

Figure 9:
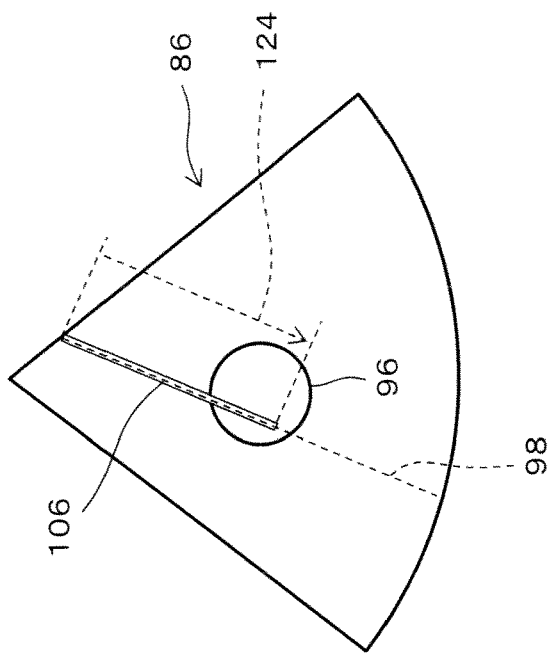
FIG. 9 is a diagram showing a second registration example of an existing insertion path.

FIG. 9 shows a second registration example of an insertion history. A user may perform, for example, a measurement of the distance and designate a length 124 of the first needle image 106 in the sectional image 86. In this way, the position of the tip of the needle is determined on the first prospective line 98.

FIG. 10 shows a third registration example of an insertion history. In the third registration example, image processing is applied. Specifically, processes such as a binarization process and segmentation process are applied to the sectional image 86 on the left. As a result of these image processes, a sectional image 86A is generated. The sectional image 86A includes a first needle image 106A extracted by the image processes. The tip position of the first needle image 106A (the coordinates of the left end tip) is automatically sensed as shown by a reference numeral 126. Alternatively, the target point (the position of the insulator, or the like) may be configured to be automatically determined as shown by a reference numeral 128.

By the registration methods described above, the information of the actual insertion length in the insertion path is registered in the insertion history storage unit. Based on such information, an existing line can be generated as a graphical image in each reference image and the sectional image.

Figure 11:
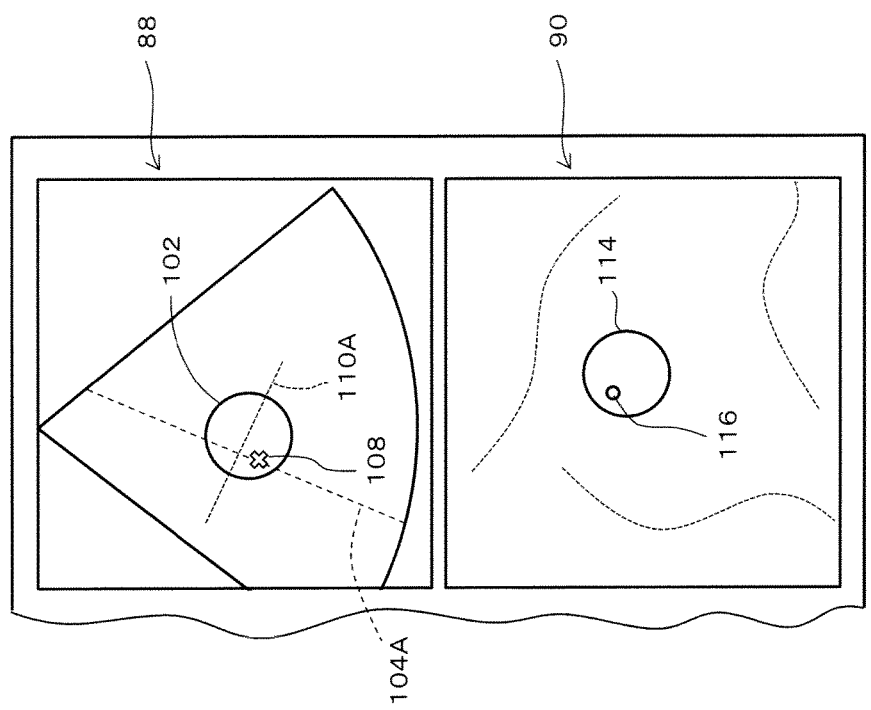
FIG. 11 is a diagram showing an example of an orthogonal sectional reference image at a position corresponding to a location where an insulator is provided.

As shown in FIG. 11, an image corresponding to a cross section cutting a position of an insulator may be generated and displayed as an orthogonal sectional image. In the corresponding sectional image 88, the mark 108 representing the tip position is displayed on the second existing line 104A. Accordingly, the insulator position can be determined. The line cutting through the insulator position is a line 110A. An orthogonal cross section corresponding to the line 110A is the orthogonal sectional image 90. In the image, a position mark 116 which represents the position of the cross section of the insertion path after insertion completion corresponding to the first existing line is displayed in the guide circle 114.

Figure 12:
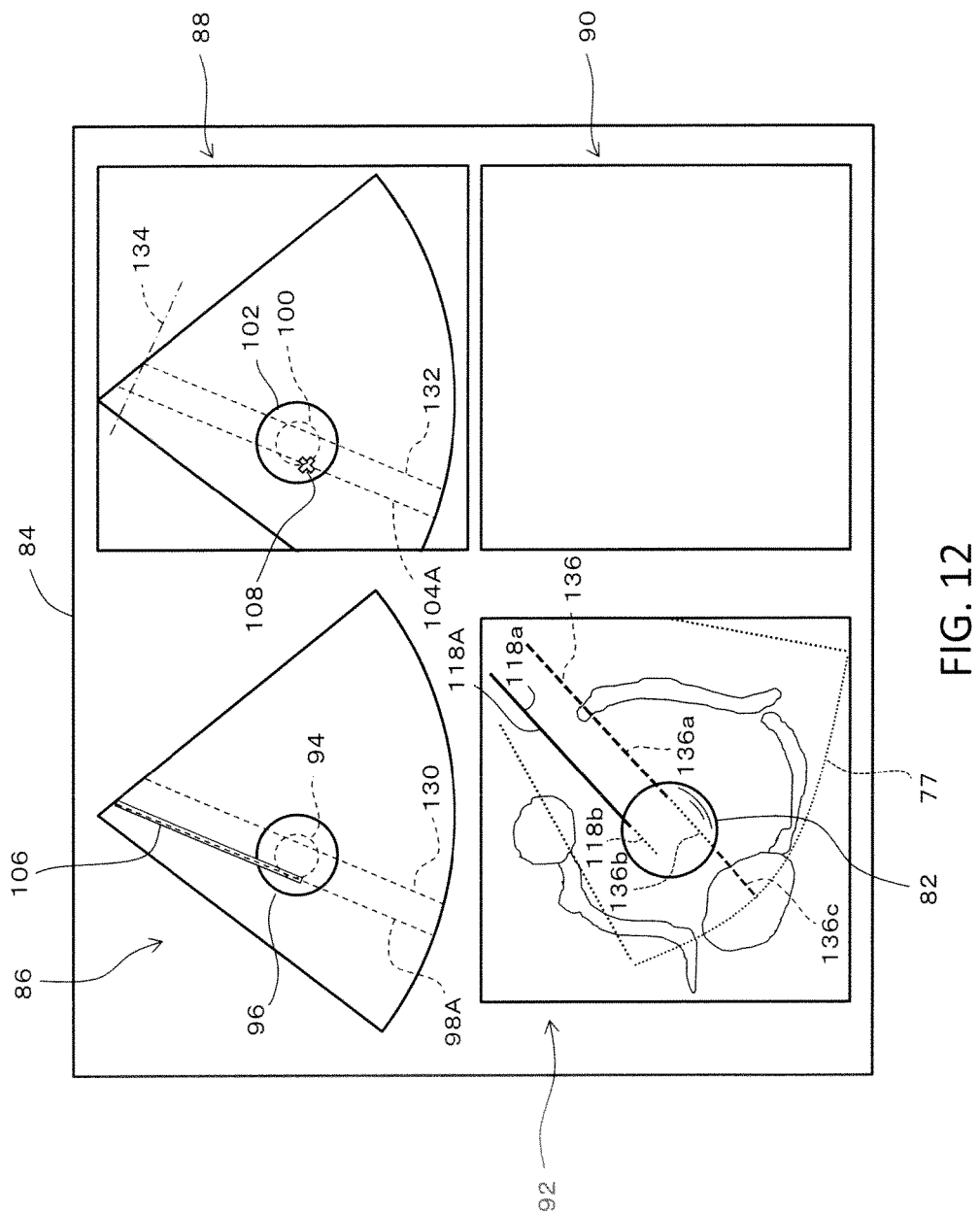
FIG. 12 is a diagram showing a display example before a second insertion.

FIG. 12 shows an example of an image which is displayed after completion of the first insertion and before the start of the second insertion. In this example, the sectional image 86 displays a first existing line 98A and a second prospective line 130. The lines 98A and 130 are positioned in parallel to each other. In this example, as a first puncture needle is positioned on the scan plane (more accurately, in the vicinity space), the first needle image 106 appears in the sectional image 86 and the first existing line 98A is displayed. For example, to maintain the display of the first needle image 106 or to continuously display the first existing line 98A, the probe position is shifted towards the scan plane while maintaining the orientation of the probe. As a result, the second prospective line 130 appears on the right side of the first existing line 98A. By maintaining the two lines 98A and 130 displayed at the same time, the second insertion path can be set in advance while checking the parallel relationship and the distance between them. This is merely one example. The second prospective line 130 is appropriately determined in accordance with the position and the shape of the target.

Although in the present embodiment the first existing line 98A is displayed in the sectional image 86, such a display is not always necessary. Conventional B-mode sectional images may be displayed. A future insertion path can be accurately set by referring to two or more reference images (in particular by the three-dimensional reference image 92).

The first existing line 104A and a second prospective line 132 are displayed also in the corresponding sectional image 88. The mark 108 representing the tip position of the puncture needle is displayed on the first existing line 104A. Reference numeral 134 represents a line showing an initial position of the orthogonal cross section. In the depicted example, the orthogonal sectional image 90 is not displayed, because the tip position of the second puncture needle has not been determined. An orthogonal sectional image corresponding to the line 134 may be displayed. In that case, it is preferable to display a projected image showing a space ahead including the orthogonal cross section.

The three-dimensional reference image 92 displays the guide ball 82 and a first existing line 118A, which consists of the portion 118b included in the guide ball and the remaining portion 118a as described above. A second prospective line 136 within the scan plane mark 77 is also displayed. The second prospective line 136 consists of a portion 136b included in the guide ball 82, a portion 136a on the proximal side of the portion 136b, and a portion 136c on the distal side from the guide ball 82. Such a three-dimensional display enables the user to intuitively and easily recognize the spatial relationship between the tissue and the lines. It should be noted, however, that such a display method is merely an example.

In the condition shown in FIG. 12, a change in the position or the orientation of the probe causes a change (or disappearance, depending on the situation) in the first existing line 98A and the first needle image 106 in the sectional image 86; a change (or disappearance, depending on the situation) in the first existing line 104A and the mark 108 in the corresponding sectional image 88; and a change in the second prospective line 136 in the three-dimensional reference image 92 (no change in the first existing line 118A). Therefore, the user determines the position and the orientation of the probe such that the first existing lines 98, 104, 118 and the second prospective lines 130, 132, 136 are positioned substantially parallel to each other with an appropriate space therebetween in the three-dimensional space. In this case, the position and the orientation of the probe may be adjusted such that, for example, the first existing line 118 passes in the vicinity of the guide ball 82 on one side, and the second prospective line 136 passes in the vicinity of the guide ball 82 on the other side. It is preferable that the size, the shape, and other characteristics of the target model as the guide ball are predetermined so as to facilitate the path setting relative to the target. In one embodiment, a cauterization area may be displayed as a target model.

Figure 13:
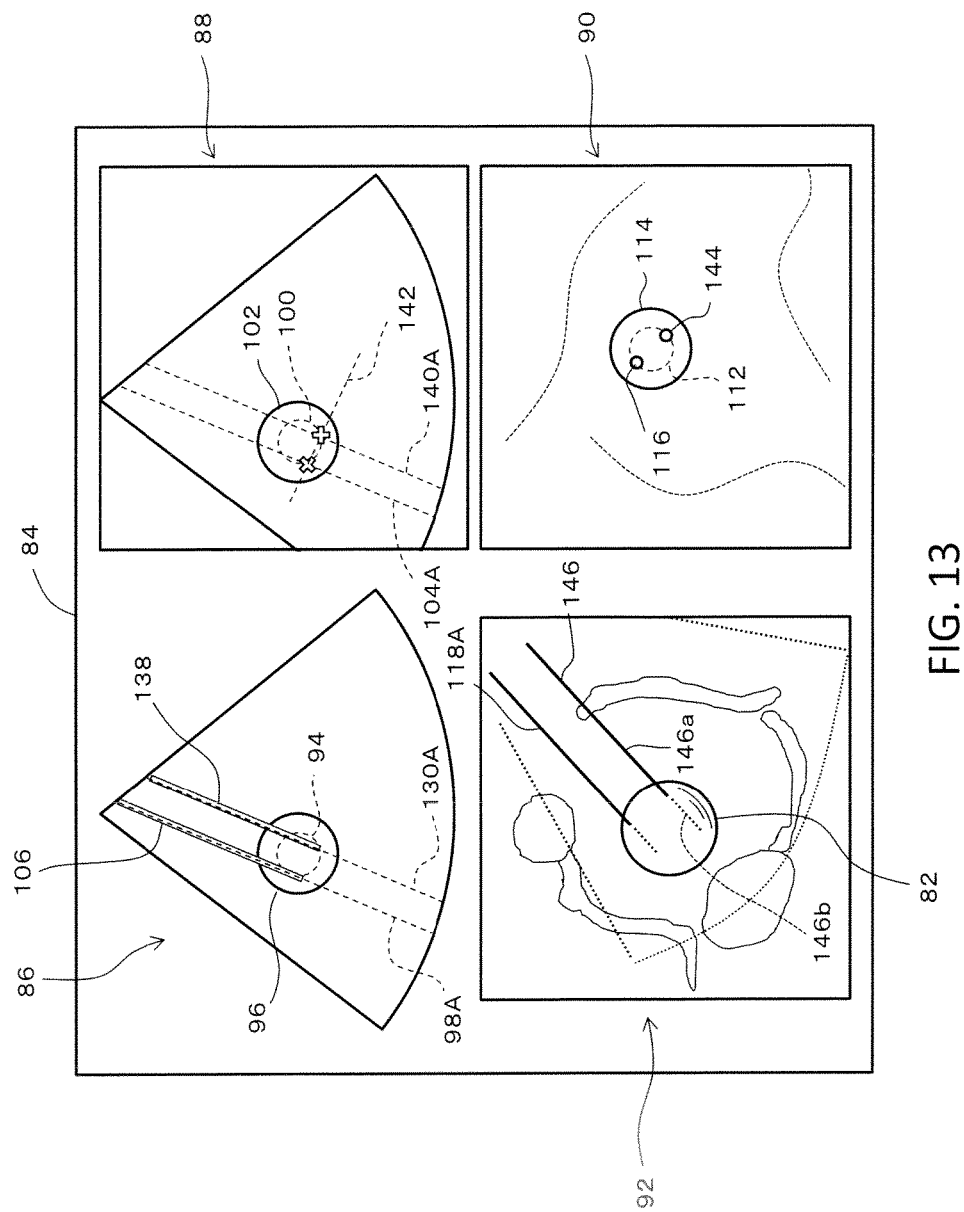
FIG. 13 is a diagram showing a display example when the second insertion is completed.

FIG. 13 shows a display example upon completion of the second insertion. In the depicted example, two puncture needles appear within the scan plane (or in the vicinity) in the actual three-dimensional space. Thus, a first existing line 98A and a second existing line 130A are displayed in parallel in the sectional image 86. Along with these lines, a first needle image 106 and a second needle image 138 appear on these lines. The tips are displayed on both sides of a target 94 such that the tips sandwich the target 94. When the first puncture needle is out of the scan plane, the first existing line 98A and the first needle image 106 are not displayed. To reduce the amount of calculation, the display of the first existing line 98A in the sectional image 86 may be omitted.

The corresponding sectional image 88 also displays the first existing line 104A and a second existing line 140A. Two marks indicating the positions of the tips of the first puncture needle and the second puncture needle are displayed on these lines. A line 142 across the marks represents the cutting position of the orthogonal cross section. The image of the orthogonal cross section is displayed as an orthogonal sectional image 90. The orthogonal sectional image 90 displays two marks 116, 144 at the position corresponding to the cross sections of the two existing lines.

In the three-dimensional reference image 92, the two existing lines 118A, 146 are displayed such that the tips of these lines are inserted into the guide ball 82. The newly-displayed second existing line 146 consists of a portion 146b which is included in the guide ball 82 and the remaining portion 146a on the proximal side of the portion 146b. The transparency of the guide ball 82 may be configured to be variable.

The above first embodiment uses the scan plane as a reference. A vicinity space including the scan plane is defined in the three-dimensional space. The existing line is displayed on each screen only when the existing insertion path is within the vicinity space. Although insertion of two puncture needles is described in the above first embodiment, similar processes are performed to display three or more puncture needles. Any of the above described configurations are merely examples, and can be varied as required for treatment purposes, treatment conditions, and needs of users.

Figure 14:
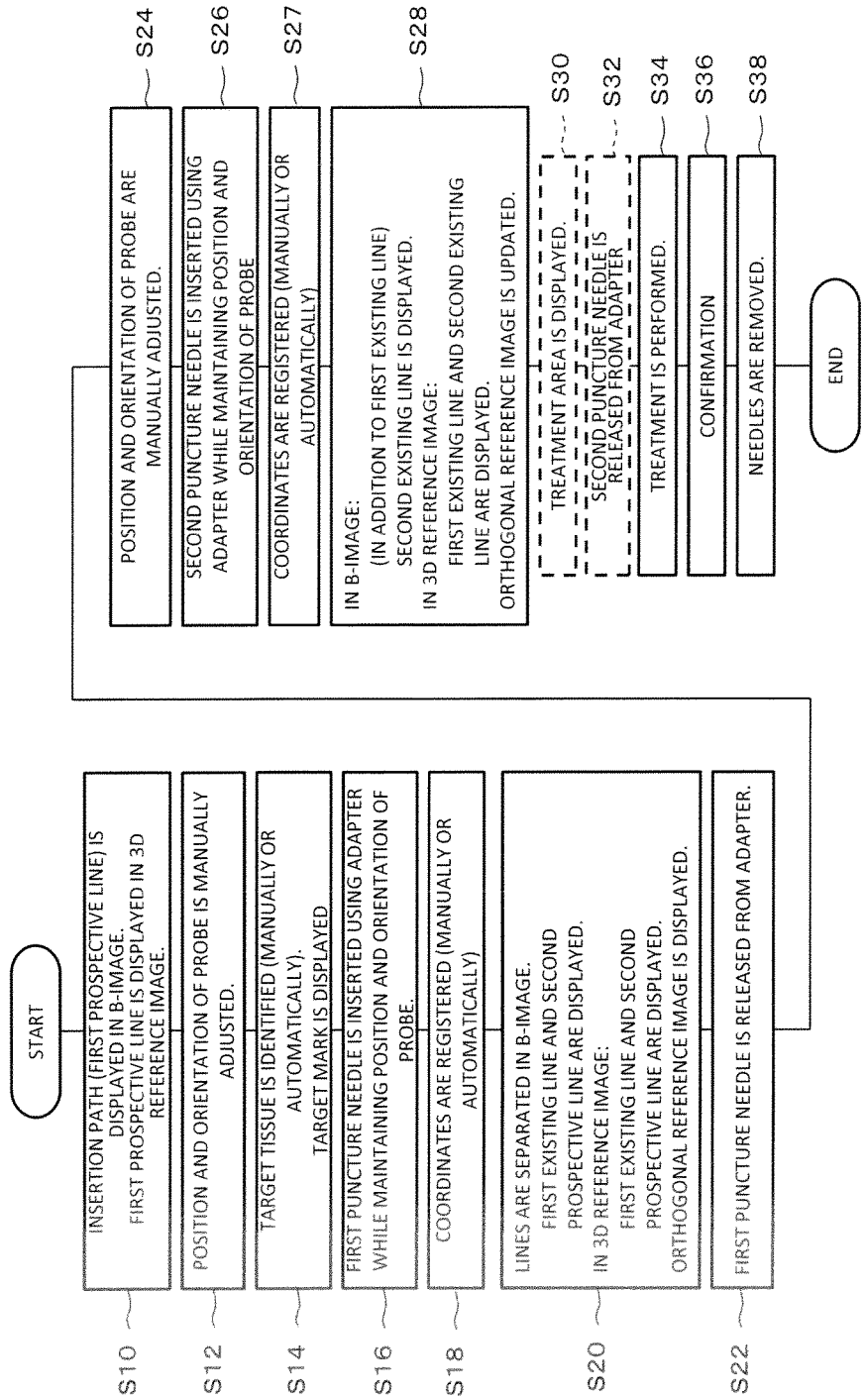
FIG. 14 is a flowchart showing operations according to the first embodiment.

The operations of the first embodiment are described below by referring to FIG. 14.

In S10, simultaneously with display of a first prospective line in a sectional image (B-mode image), the first prospective line is also displayed in a three-dimensional image (3D image). In S12, with the first prospective line displayed as described above, the position and the orientation of the probe are manually adjusted such that the target and the first prospective line are correctly positioned relative to each other.

In S14, when a target tissue is identified by a user or automatically in the three-dimensional reference image, the sectional image, or the corresponding sectional image, a guide ball or a guide circle is displayed accordingly. For example, when two puncture needles are used for the insertion, if the spatial distance between the two puncture needles is predetermined, the diameter of the guide ball can be set equal to the distance. Alternatively, the guide ball may be set to have a diameter greater than the predetermined distance such that the two insertion paths finally pass through the guide ball on respective sides.

When the position and the orientation of the probe are determined, an insertion of the first puncture needle is performed using a puncture adapter while maintaining the position and the orientation of the probe. In this case, the insertion is performed while referring to the sectional image and the three-dimensional reference image until the tip of the puncture needle is at a correct position relative to the target tissue or the guide ball. In S18, the insertion history is registered by the user or automatically when insertion completion is confirmed. In other words, current coordinate information is registered. Although the puncture needle may be set in the puncture adapter during the adjustment process of the position and the orientation of the probe (but before the insertion), the probe can be more freely moved by setting the puncture needle in the adapter after the adjustment of the position and the orientation of the probe.

In S20, upon registration of the insertion history, a line separation process is performed in the sectional images. Specifically, the first existing line and the second prospective line are displayed in the sectional images. In the initial state, both lines are displayed to be overlapped with each other. Therefore, in consideration of the appearance, the start of the display of either one of the lines may be delayed until after movement of the probe. Similarly to the sectional images, the first existing line and the second prospective line are displayed in the three-dimensional reference image. Also in this image, both lines are displayed to be overlapped with each other in the initial state. The display of the orthogonal reference image is also started. Further, in S22, the first puncture needle is released from the puncture adapter. In this way, insertion of the second puncture needle is prepared.

In S24, the position and the orientation of the probe are manually adjusted in consideration of the positional relationship with the target or the guide ball by referring to the sectional images and the three-dimensional reference image. In this case, the position and the orientation of the probe are adjusted such that, for example, the second prospective line is parallel to the first existing line with a certain distance therebetween.

When the adjustment of the position and the orientation of the probe is completed, insertion of the second puncture needle is performed in S26 using the puncture adapter while maintaining the position and the orientation of the probe.

When the insertion is completed, the insertion history registration process is performed in S27.

This registration process causes the display of the second existing line in the sectional images in S28. In this case, when the first puncture needle resides within the scan plane, the first-existing line is also displayed in the sectional images. The three-dimensional reference image displays the first existing line and the second existing line. Further, the orthogonal reference image is updated. During the high-frequency treatment, the reference to an image including such graphical images allows confirmation of appropriate positioning of the two puncture needles relative to the target.

At this stage, a treatment area may be displayed in the three-dimensional reference image as shown in S30 and described in a second embodiment below. In S32, a second puncture needle may be released from the puncture adapter as required. Next, in S34, high-frequency treatment is performed. In S36, status after the treatment is confirmed through images such as a sectional image. In S38, the two puncture needles are removed from the living body. The operations (or the procedure flow) in FIG. 14 are merely examples.

Next, the second embodiment is described by referring to FIGS. 15 to 20. In each drawing described below, elements similar to those in the first embodiment are represented by identical reference numerals, and the description of these elements is omitted.

Figure 15:
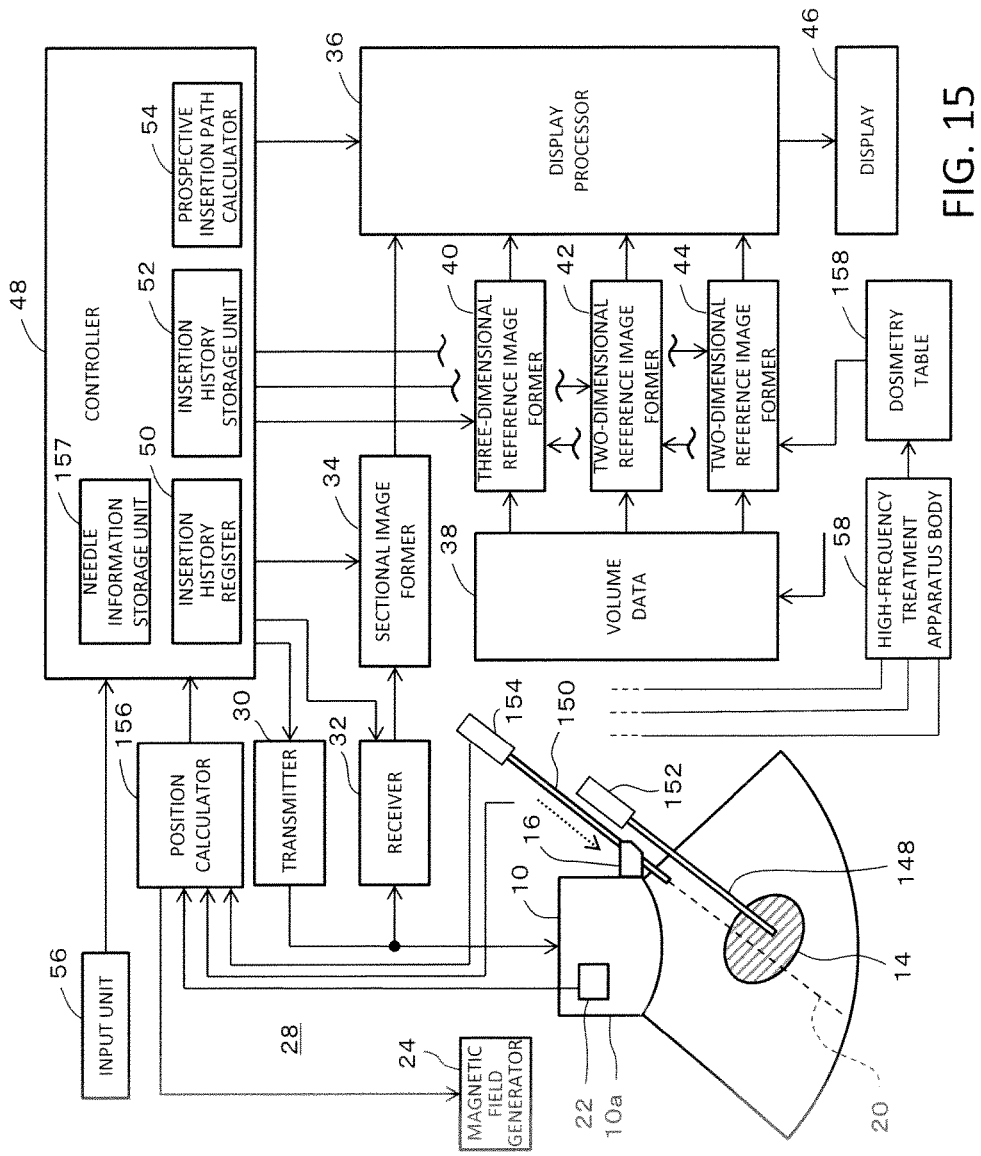
FIG. 15 is a block diagram showing a configuration of an ultrasonic diagnostic system according to a second embodiment.

In the example shown in FIG. 15, two puncture needles 148, 150 are described. Reference numeral 148 represents a first puncture needle after insertion completion. Reference numeral 150 represents a second puncture needle for subsequent insertion. In this example, the puncture needles 148, 150 respectively include sensors 152, 154. The sensors 152, 154 are magnetic sensors similar to the above described magnetic sensor 22. The sensors 152, 154 respectively obtain the position information of the puncture needles 148, 150. Specifically, signals from the sensors 152, 154 are sent to a position calculator 156, where the position information (the position and the orientation in the three-dimensional space) is calculated for each of the puncture needles.

In this way, the depth information can be obtained at any time in the insertion process with the puncture needles in the living body, that is, the orthogonal sectional image can be updated in real time. The position of the tip can be determined based on the amount of insertion when a predetermined user input is performed at the time of insertion completion. Based on the position information, the insertion history register 50 registers required information in the insertion history storage unit 52.

A needle information storage unit 157 stores the size, the electrode length, and the electrode array of each puncture needle, in addition to the number of the puncture needles to be used. An automatic calculation of treatment area is enabled by referring to such needle information and a dosimetry table 158 described below. The high-frequency treatment apparatus body 58 supplies high-frequency signals to the respective puncture needles. The high-frequency treatment apparatus body 58 also includes a cooling mechanism. The dosimetry table 158 stores information about the treatment area which is determined based on the information such as the number of the puncture needles, the needle array, and the applied electrodes. Therefore, the treatment area in the three-dimensional space can be determined by referring to the dosimetry table 158 based on the current needle array and the needle information. The determined treatment area can be displayed in the three-dimensional reference image as a graphic image.

Figure 16:
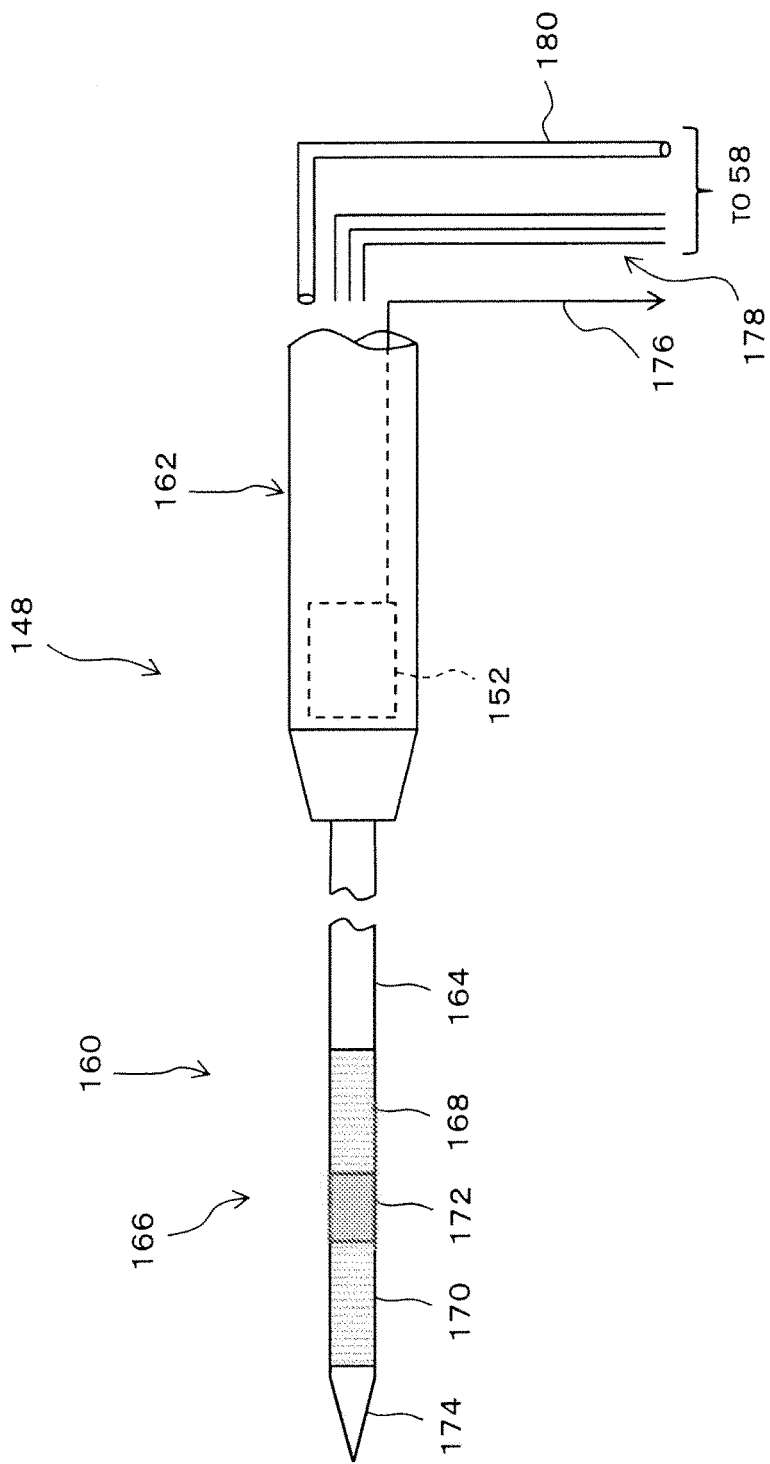
FIG. 16 is a diagram showing an example of a puncture needle for medical treatment according to the second embodiment.

FIG. 16 shows an example of a puncture needle according to the second embodiment. The puncture needle 148 is a treatment tool which consists of an insertable portion 160 and an outside body portion 162. The insertable portion 160 includes a tip portion 166 where a pair of electrodes 168, 170 is disposed with an insulator 172 positioned therebetween. Reference numeral 174 represents a tip. A magnetic sensor 152 is disposed in the outside body portion (operation portion) 162. Signals 176 are output from the magnetic sensor 152. The signals 176 are output to the position calculator 156 shown in FIG. 15. Further, high-frequency signals are supplied from the high-frequency treatment apparatus body to each of the electrodes as represented by reference numeral 178. A pipe for transporting a cooling medium is disposed as represented by reference numeral 180. The tip portion 166 is cooled by the cooling medium. Although two cooling pipes, a feeding pipe and a returning pipe, are disposed, FIG. 16 shows one of the two pipes by reference numeral 180.

Figure 17:
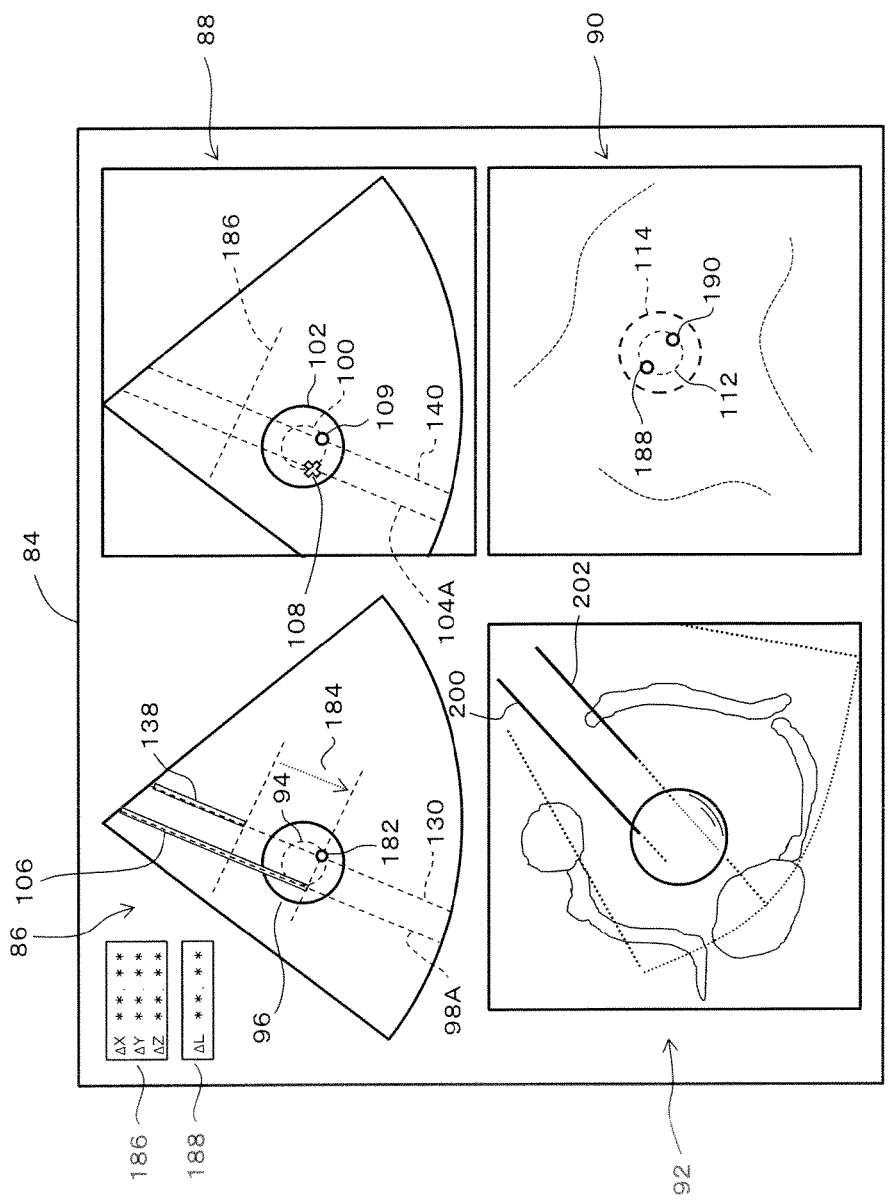
FIG. 17 is a diagram showing a display example according to the second embodiment.

FIG. 17 shows a display example according to the second embodiment. The display shows a view during the second insertion. A sectional image 86 displays a first existing line 98A and a second prospective line 130. A first needle image 106 appears on the first existing line 98A, and a second needle image 138 of the second puncture needle which is inserted halfway appears on the second prospective line 130. In the depicted example, the target point on the second prospective line 130 is calculated based on the registered information of the insertion history of the first puncture needle. The target point is shown by a mark 182. In this case, the target point is determined such that, for example, the tips of the two puncture needles are aligned. The user can continue the insertion until the tip of the second needle image 138 reaches the mark 182. Reference numeral 184 represents the distance from the tip of the puncture needle to the target point. As represented by reference numeral 186, coordinate information showing spatial relationship between the two puncture needles may be calculated and displayed on the screen. For example, the distance between the two puncture needles on each axis may be displayed in numerals. Further, the above described distance 184 may be displayed as numerals as represented by reference numeral 188.

The corresponding sectional image 88 shows a first existing line 104A, a second prospective line 140, a mark 108 showing the tip position of the first puncture needle, and a mark 109 showing the target point on the second prospective line 140. In addition, reference numeral 100 represents a target image and reference numeral 102 represents a guide circle showing a cross section of the guide ball. Reference numeral 186 represents a line representing the cutting position of the orthogonal cross section.

The orthogonal sectional image 90 displays a mark 188 showing the position of the cross section of the first existing line and a mark 190 showing the position of the cross section of the first prospective line. In the orthogonal sectional image 90, a projected image may be displayed. In such a display configuration, a target image 112 can be displayed in the orthogonal sectional image 90. Further, a guide circle 114 corresponding to the guide ball may also be displayed.

A three-dimensional reference image 92 displays a first existing line 200 and a second prospective line 202. In this example, the tip positions of the puncture needles are represented by different line types. Also in the second embodiment, under assumption that the puncture needle is guided by the puncture adapter, an appropriate insertion preparation for the second puncture needle can be performed by optimizing the position of the second prospective line of the second puncture needle for subsequent insertion while referring to the first existing line representing the first puncture needle after insertion completion, in other words, by determining the position and the orientation of the probe such that the two lines are appropriately positioned relative to each other. Under such conditions, insertion of the second puncture needle while maintaining the position and the orientation of the probe enables safe and easy positioning of the second puncture needle relative to the first puncture needle. Of course, safety can be ensured also after the start of the insertion, because the path of the second puncture needle can be checked in the sectional image and the three-dimensional reference image during the insertion of the second puncture needle.

Figure 18:
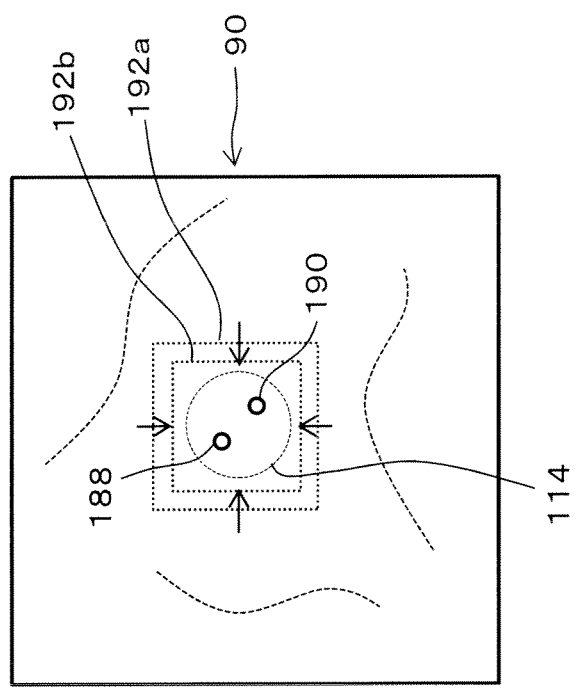
FIG. 18 is a diagram showing an example of a distance display in an orthogonal sectional reference image.

FIG. 18 shows an example of an orthogonal sectional image 90. In this drawing, reference numeral 188 represents a mark showing the position of the cross section of the first existing line. Reference numeral 190 represents a mark showing the position of the cross section of the second prospective line. In such an orthogonal sectional image, it is not possible to intuitively recognize the distance between the target and the second puncture needle. Therefore, as represented by reference numerals 192a, 192b, a rectangular box may be displayed such that the size of the box changes in accordance with the distance between the tip of the puncture needle and the center of the target. Specifically, the distance is made intuitively recognizable by reducing the size of the box as the distance becomes shorter. Of course, such a graphic display is merely an example of a distance display.

Figure 19:
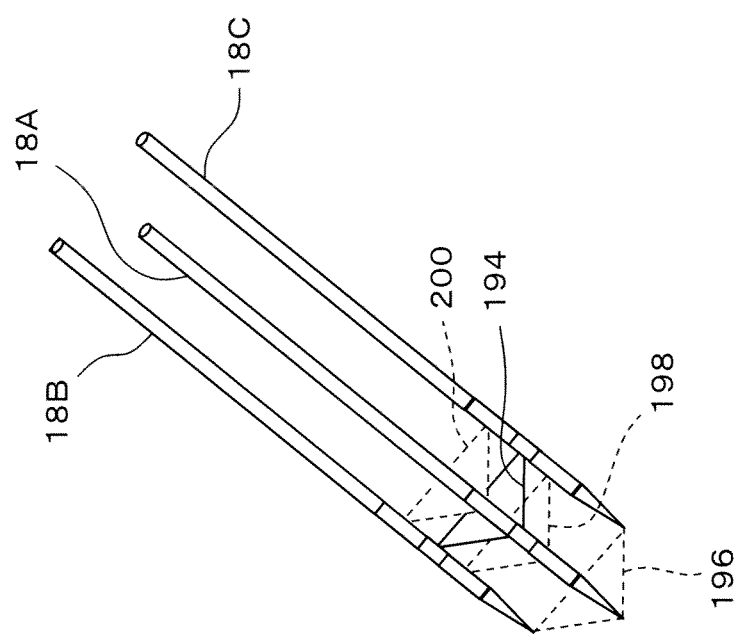
FIG. 19 is a diagram showing a display example of a diagram depicting a puncture needle array.

FIG. 19 shows an example display of a puncture needle array in the three-dimensional reference image. This example includes three needles 18A, 18B, and 18C. A triangle such as the one represented by a reference numeral 194 connecting the central axes of the three needles may be displayed to enable intuitive recognition of the positional relationship among the three needles viewed in an oblique direction. In this example, the centers of the insulators of the puncture needles are connected by linear lines. As a result, the triangle diagram 194 is formed. The diagram 194 is displayed as a diagram in the three-dimensional reference image. In the place of or together with the diagram 194, a diagram 196 connecting the three tips may be displayed. In addition, diagrams 198, 200 connecting the respective electrodes may be displayed. Such graphical displays enable intuitive and easy recognition of spatial relationships.

Figure 20:
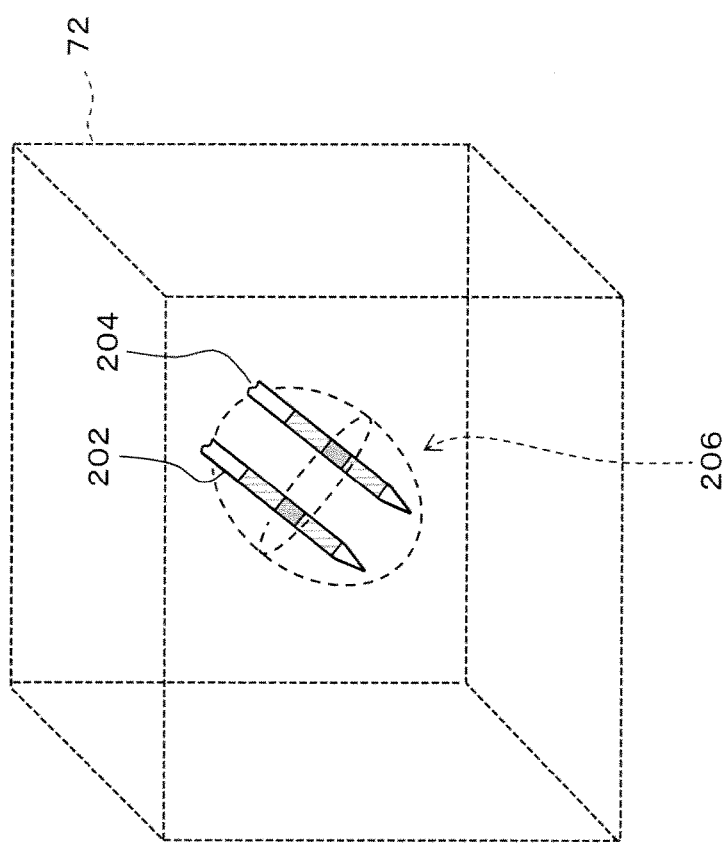
FIG. 20 is a diagram showing a display example of a treatment area in a three-dimensional image.

FIG. 20 shows a display example of a treatment area in a three-dimensional reference image 72. For example, with two needle images 202, 204 being displayed, a treatment area 206 may be displayed as a graphic or a diagram surrounding the needle images. In this case, the above described dosimetry table is referred to such that the treatment area is calculated and displayed based on the dosimetry table.

Although puncture needles in the above described embodiments are assumed to be treatment tools, similar configurations may be applied to a case where two or more puncture needles of other types are inserted. Further, a puncture guide which can guide two or more puncture needles may be used.

The invention claimed is:
1. A medical system comprising:
a probe comprising a puncture adapter that sequentially guides a plurality of puncture needles that are inserted into a three-dimensional space in a living body, the probe outputting reception signals by transmitting and receiving ultrasonic waves to and from the three-dimensional space;
a calculator that calculates a prospective insertion path based on position information obtained for the probe;
a register that registers an existing insertion path based on at least one of the position information of the puncture needle at time of insertion completion and the prospective insertion path;
an ultrasonic image generator that generates a two-dimensional sectional image representing a beam scan plane as an ultrasonic image based on the reception signals, the ultrasonic image generator displaying a prospective insertion path symbol representing the prospective insertion path in the two-dimensional sectional image, the ultrasonic image generator further displaying an existing insertion path symbol in the two-dimensional sectional image based on the existing insertion path of the puncture needle when the puncture needle after insertion completion is in a vicinity space of the beam scan plane; and a three-dimensional reference image generator comprising a unit that forms a three-dimensional ultrasonic image based on volume data obtained from the three-dimensional space, the three-dimensional reference image generator generating a three-dimensional reference image comprising the three-dimensional ultrasonic image, a three-dimensional existing insertion path symbol representing the existing insertion path of a puncture needle after insertion completion, and a three-dimensional prospective insertion path symbol representing the prospective insertion path of a puncture needle for subsequent insertion, wherein the prospective insertion path symbol is unmovable in the two-dimensional sectional image, and the three-dimensional existing insertion path symbol is unmovable in the three-dimensional reference image.

2. The system according to claim 1, wherein in an adjustment process after previous insertion completion and before start of next insertion, when a position and an orientation of the probe are changed, a position and an orientation of the three-dimensional prospective insertion path symbol are changed, while maintaining a position and an orientation of the three-dimensional existing insertion path symbol in the three-dimensional reference image, and the next insertion using the puncture adapter is performed after completion of the adjustment of the position and the orientation of the probe.

3. The medical system according to claim 2, wherein the probe forms a beam scan plane traversing the three-dimensional space, the three-dimensional reference image further comprises a scan plane symbol representing the beam scan plane, and the three-dimensional prospective insertion path symbol is displayed within the scan plane symbol in the three-dimensional reference image.

4. The medical system according to claim 3, wherein the three-dimensional reference image further comprises a target symbol corresponding to or including a target image.

5. The medical system according to claim 1, wherein the medical system further comprises an orthogonal sectional image generator that generates an orthogonal sectional image representing a cross section orthogonal to the prospective insertion path, and the orthogonal sectional image includes a position mark representing the existing insertion path and another position mark representing the prospective insertion path.

6. The medical system according to claim 5, wherein the medical system further comprises a sensor that senses information usable to determine an amount of insertion for a puncture needle for subsequent insertion, and a position of the orthogonal cross section on the prospective insertion path is changed according to the information sensed by the sensor.

7. The medical system according to claim 1, wherein after registration of the existing insertion path, when the existing insertion path departs from the prospective insertion path, display of a prospective insertion path symbol representing a next prospective insertion path starts in the two-dimensional sectional image and display of a three-dimensional prospective insertion path symbol representing a next prospective insertion path starts in the three-dimensional reference image.

8. The medical system according to claim 1, wherein the register registers the existing insertion path based on information entered by a user who has referred to a puncture needle image in the ultrasonic image.

9. The medical system according to claim 1, wherein the register registers the existing insertion path based on signals from sensors disposed on the respective puncture needles.

10. The medical system according to claim 1, wherein the puncture needles are high-frequency treatment tools, and high-frequency signals are supplied to an electrode array of the plurality of puncture needles inserted in the three-dimensional space.

11. The medical system according to claim 10, wherein the medical system further comprises a unit to display, in the three-dimensional image, a treatment area symbol representing a treatment area of the plurality of puncture needles.

* * * * *